US010214782B2

(12) United States Patent
Bowers et al.

(10) Patent No.: US 10,214,782 B2
(45) Date of Patent: Feb. 26, 2019

(54) METHODS AND KITS TO IDENTIFY KLEBSIELLA STRAINS

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: Jolene Bowers, Flagstaff, AZ (US); Elizabeth Driebe, Flagstaff, AZ (US); David Engelthaler, Flagstaff, AZ (US); Paul Keim, Flagstaff, AZ (US)

(73) Assignees: The Translational Genomics Research Institute, Phoenix, AZ (US); Arizona Board of Regents on Behalf of Northern Arizona University, Flagstaff, AZ (US)

( * ) Notice: Subject to any disclaimer, the term of this patent is extended or adjusted under 35 U.S.C. 154(b) by 31 days.

(21) Appl. No.: 15/214,709

(22) Filed: Jul. 20, 2016

(65) Prior Publication Data

US 2017/0022543 A1 Jan. 26, 2017

Related U.S. Application Data

(60) Provisional application No. 62/195,206, filed on Jul. 21, 2015.

(51) Int. Cl.
*C12Q 1/68* (2018.01)
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS 6,610,836 B1 * 8/2003 Breton .................. C07K 14/26 435/320.1

OTHER PUBLICATIONS

Veleba, et al. Characterization of RarA, a novel AraC family multidrug resistance regulator in Klebsiella pneumoniae. Antimicrob Agents Chemother. 2012;56(8):4450-8. doi: 10.1128/AAC.00456-12. PubMed PMID: 22644028; PubMed Central PMCID: PMC3421627.
Frank, et al. Klebsiella pneumoniae targets an EGF receptor-dependent pathway to subvert inflammation. Cellular microbiology. 2013;15(7):1212-33. doi: 10.1111/cmi.12110. PubMed PMID: 23347154.
Segura, Mariela. Fisher scientific award lecture—the capsular polysaccharides of Group B *Streptococcus* and *Streptococcus suis* differently modulate bacterial interactions with dendritic cells. Canadian journal of microbiology. 2012;58(3):249-60. doi: 10.1139/w2012-003. PubMed PMID: 22356626.
Lin, et al. Outer membrane proteins: key players for bacterial adaptation in host niches. Microbes and infection / Institut Pasteur. 2002;4(3):325-31. PubMed PMID: 11909743.
March, et al. Role of bacterial surface structures on the interaction of Klebsiella pneumoniae with phagocytes. PLoS One. 2013;8(2):e56847. doi: 10.1371/journal.pone.0056847. PubMed PMID: 23457627; PubMed Central PMCID: PMC3574025.
Smith, et al. A molecular Swiss army knife: OmpA structure, function and expression. FEMS microbiology letters. 2007;273(1):1-11. doi: 10.1111/j.1574-6968.2007.00778.x. PubMed PMID: 17559395.
Garcia-Sureda, et al. OmpK26, a novel porin associated with carbapenem resistance in Klebsiella pneumoniae. Antimicrob Agents Chemother. 2011;55(10):4742-7. doi:10.1128/AAC.00309-11. PubMed PMID: 21807980; PubMed Central PMCID: PMC3186958.
Kitchel, et al. Genetic factors associated with elevated carbapenem resistance in KPC-producing Klebsiella pneumoniae. Antimicrob Agents Chemother. 2010;54(10):4201-7. Epub Jul. 28, 2010. doi: AAC.00008-10 [pii] 10.1128/AAC.00008-10. PubMed PMID: 20660684; PubMed Central PMCID: PMC2944623.
Domenech-Sanchez, et al. Role of Klebsiella pneumoniae OmpK35 porin in antimicrobial resistance. Antimicrob Agents Chemother. 2003;47(10):3332-5. PubMed PMID: 14506051; PubMed Central PMCID: PMC201126.
Kaczmarek, et al. High-level carbapenem resistance in a Klebsiella pneumoniae clinical isolate is due to the combination of bla(ACT-1) beta-lactamase production, porin OmpK35/36 insertional inactivation, and down-regulation of the phosphate transport porin phoe. Antimicrob Agents Chemother. 2006;50(10):3396-406. doi: 10.1128/AAC.00285-06. PubMed PMID: 17005822; PubMed Central PMCID: PMC1610099.
Croucher, et al. The emergence of bacterial "hopeful monsters". MBio. 2014;5(4):e01550-14. doi: 10.1128/mBio.01550-14. PubMed PMID: 25073645; PubMed Central PMCID: PMC4128365.
Souli, et al. An outbreak of infection due to beta-Lactamase Klebsiella pneumoniae Carbapenemase 2-producing K. pneumoniae in a Greek University Hospital: molecular characterization, epidemiology, and outcomes. Clin Infect Dis. 2010;50(3):364-73. doi: 10.1086/649865. PubMed PMID: 20041768.
America TSfHEo. Large Veteran Health Administration Study Shows 'Last Resort' Antibiotics Use on the Rise Dallas, TX2011 [cited Aug. 12, 2014]. Available from: http://www.shea-online.org/View/smid/428/ArticleID/72.aspx.
Tsai, et al. Klebsiella pneumoniae outer membrane porins OmpK35 and OmpK36 play roles in both antimicrobial resistance and virulence. Antimicrob Agents Chemother. 2011;55(4):1485-93. doi: 10.1128/AAC.01275-10. PubMed PMID: 21282452; PubMed Central PMCID: PMC3067157.

(Continued)

*Primary Examiner* — Aaron A Priest
*Assistant Examiner* — Olayinka A Oyeyemi

(57) ABSTRACT

Embodiments of the invention provide a method of detecting one or more strains of *Klebsiella pneumoniae*. The method may include forming a plurality of mixtures for nucleic amplification. The method can include amplification of specific sequences within the *K. pneumonia* genome that can provide definitive information to distinguish between one or more types or strains of *K. pneumonia.*

18 Claims, 8 Drawing Sheets

Specification includes a Sequence Listing.

(56) References Cited

OTHER PUBLICATIONS

Holt, K. SRST2 Short Read Sequence Typing for Bacterial Pathogens: GitHub; 2013 [updated Feb. 6, 2014; cited Mar. 1, 2014]. Available from: https://github.com/katholt/srst2.
McKenna, et al. The Genome Analysis Toolkit: a MapReduce framework for analyzing next-generation DNA sequencing data. Genome Res. 2010;20(9):1297-303. doi: 10.1101/gr.107524.110. PubMed PMID: 20644199; PubMed Central PMCID: PMC2928508.
Tamura, et al. MEGA5: molecular evolutionary genetics analysis using maximum likelihood, evolutionary distance, and maximum parsimony methods. Mol Biol Evol. 2011;28(10):2731-9. Epub May 7, 2011. doi: msr121 [pii] 10.1093/molbev/msr121. PubMed PMID: 21546353; PubMed Central PMCID: PMC3203626.
Paradis, et al. APE: Analyses of Phylogenetics and Evolution in R language. Bioinformatics. 2004;20(2):289-90. PubMed PMID: 14734327.
Letunic, et al. Interactive Tree of Life v2: online annotation and display of phylogenetic trees made easy. Nucleic acids research. 2011;39(Web Server issue):W475-8. doi: 10.1093/nar/gkr201. PubMed PMID: 21470960; PubMed Central PMCID: PMC3125724.
Drummond, et al. Bayesian phylogenetics with BEAUti and the BEAST 1.7. Mol Biol Evol. 2012;29(8):1969-73. Epub Mar. 1, 2012. doi: 10.1093/molbev/mss075. PubMed PMID: 22367748; PubMed Central PMCID: PMC3408070.
Carattoli, et al. PlasmidFinder and pMLST: in silico detection and typing of plasmids. Antimicrob Agents Chemother. 2014. doi: 10.1128/AAC.02412-14. PubMed PMID: 24777092.
Zankari, et al. Identification of acquired antimicrobial resistance genes. J Antimicrob Chemother. 2012;67(11):2640-4. doi: 10.1093/jac/dks261. PubMed PMID:22782487; PubMed Central PMCID: PMC3468078.
Bankevich, et al. SPAdes: a new genome assembly algorithm and its applications to single-cell sequencing. Journal of computational biology : a journal of computational molecular cell biology. 2012;19(5):455-77. doi: 10.1089/cmb.2012.0021. PubMed PMID:22506599; PubMed Central PMCID: PMC3342519.
Bolger, et al. Trimmomatic: A flexible trimmer for Illumina Sequence Data. Bioinformatic,s. 2014. doi: 10.1093/bioinformatics/btu170. PubMed PMID: 24695404.
Geneious. Available from Biomatters Ltd. http://www.geneious.com. 2013.
Pan, et al. Identification of Capsular Types in Carbapenem-Resistant Klebsiella pneumoniae Strains by wzc Sequencing and Implications for Capsule Depolymerase Treatment. Antimicrob Agents Chemother. 2015;59(2):1038-47. doi: 10.1128/AAC.03560-14. PubMed PMID: 25451047.
Brisse, et al. wzi Gene sequencing, a rapid method for determination of capsular type for Klebsiella strains. J Clin Microbiol. 2013;51(12):4073-8. doi: 10.1128/JCM.01924-13. PubMed PMID: 24088853; PubMed Central PMCID: PMC3838100.
Wilkinson, et al. Ligand-responsive transcriptional regulation by members of the MarR family of winged helix proteins. Current issues in molecular biology. 2006;8(1):51-62. PubMed PMID: 16450885.
Centers for Disease Control and Prevention. Antibiotic Resistance Threats in the United States, 2013. Centers for Disease Control and Prevention, 2013.
Jacob, et al. Vital Signs: Carbapenem-Resistant Enterobacteriaceae. MMWR Morb Mortal Wkly Rep. 2013;62.
Patel, et al. Outcomes of carbapenem-resistant Klebsiella pneumoniae infection and the impact of antimicrobial and adjunctive therapies. Infection control and hospital epidemiology : the official journal of the Society of Hospital Epidemiologists of America. 2008;29(12)1099-106. doi: 10.1086/592412. PubMed PMID: 18973455.
Yigit, et al. Novel carbapenem-hydrolyzing beta-lactamase, KPC-1, from a carbapenem-resistant strain of Klebsiella pneumoniae. Antimicrob Agents Chemother. 2001;45(4):1151-61. Epub Mar. 21, 2001. doi: 10.1128/AAC.45.4.1151-1161.2001. PubMed PMID: 11257029; PubMed Central PMCID: PMC90438.
Brink, et al. Emergence of New Delhi metallo-beta-lactamase (NDM-1) and Klebsiella pneumoniae carbapenemase (KPC-2) in South Africa. J Clin Microbiol. 2012;50(2):525-7. doi: 10.1128/JCM.05956-11. PubMed PMID: 22116157; PubMed Central PMCID: PMC3264190.
Munoz-Price, et al. Clinical epidemiology of the global expansion of Klebsiella pneumoniae carbapenemases. The Lancet infectious diseases. 2013;13(9):785-96. doi:10.1016/S1473-3099(13)70190-7. PubMed PMID: 23969216.
Chen, et al. Overview of the epidemiology and the threat of Klebsiella pneumoniae carbapenemases (KPC) resistance. Infection and drug resistance. 2012;5:133-41. doi: 10.2147/IDR.S26613. PubMed PMID:23055754; PubMed Central PMCID: PMC3460674.
Bialek-Davenet, et al. Genomic definition of hypervirulent and multidrug-resistant Klebsiella pneumoniae clonal groups. Emerg Infect Dis. 2014;20(11):1812-20. doi:10.3201/eid2011.140206. PubMed PMID: 25341126; PubMed Central PMCID: PMC4214299.
Voulgari, et al. The Balkan region: NDM-1-producing Klebsiella pneumoniae ST11 clonal strain causing outbreaks in Greece. J Antimicrob Chemother. 2014. doi:10.1093/jac/dku105. PubMed PMID: 24739146.
Pena, et al. Carbapenemase-producing Enterobacteriaceae in a tertiary hospital in Madrid, Spain: high percentage of colistin resistance among VIM-1-producing Klebsiella pneumoniae ST11 isolates. Int J Antimicrob Agents. 2014. doi: 10.1016/j.ijantimicag.2014.01.021. PubMedPMID: 24657043.
Lascols, et al. Surveillance and molecular epidemiology of Klebsiella pneumoniae isolates that produce carbapenemases: first report of OXA-48-like enzymes in North America. Antimicrob Agents Chemother. 2013;57(1):130-6. doi: 10.1128/AAC.01686-12. PubMed PMID:23070171; PubMed Central PMCID: PMC3535978.
Woodford, et al. Multiresistant Gram-negative bacteria: the role of high-risk clones in the dissemination of antibiotic resistance. FEMS microbiology reviews. 2011;35(5):736-55. doi: 10.1111/j.1574-6976.2011.00268.x. PubMed PMID: 21303394.
Grundmann, et al. Carbapenem-non-susceptible Enterobacteriaceae in Europe: conclusions from a meeting of national experts. Euro surveillance : bulletin Europeen sur les maladies transmissibles = European communicable disease bulletin. 2010;15(46). PubMed PMID: 21144429.
Chmelnitsky, et al. Unique genes identified in the epidemic extremely drug-resistant KPC-producing Klebsiella pneumoniae sequence type 258. J Antimicrob Chemother. 2013;68(1):74-83. Epub Oct. 9, 2012. doi: 10.1093/jac/dks370. PubMed PMID: 23042812.
Deleo, et al. Molecular dissection of the evolution of carbapenem-resistant multilocus sequence type 258 Klebsiella pneumoniae. Proc Natl Acad Sci U S A. 2014. Epub Mar. 19, 2014. doi: 10.1073/pnas.1321364111. PubMed PMID: 24639510.
Adler, et al. Development and validation of a multiplex PCR assay for identification of the epidemic ST-258/512 KPC-producing Klebsiella pneumoniae clone. Diagn Microbiol Infect Dis. 2014;78(1):12-5. doi: 10.1016/j.diagmicrobio.2013.10.003. PubMed PMID:24231383.
Gaiarsa, et al. Genomic epidemiology of Klebsiella pneumoniae: the Italian scenario, and novel insights into the origin and global evolution of resistance to carbapenem antibiotics. Antimicrob Agents Chemother. 2014. doi: 10.1128/AAC.04224-14. PubMed PMID:25367909.
Wyres, et al. Extensive capsule locus variation and large-scale genomic recombination within the Klebsiella pneumoniae clonal group 258. Genome Biol Evol. 2015. doi:10.1093/gbe/evv062. PubMed PMID: 25861820.
Croucher, et al. Bacterial genomes in epidemiology—present and future. Philosophical transactions of the Royal Society of London Series B, Biological sciences. 2013;368(1614):20120202. doi:10.1098/rstb.2012.0202. PubMed PMID: 23382424; PubMed Central PMCID: PMC3678326.
Chen, et al. Epidemic Klebsiella pneumoniae ST258 Is a Hybrid Strain. MBio. 2014;5(3). doi: 10.1128/mBio.01355-14. PubMed PMID: 24961694; PubMed Central PMCID: PMC4073492.
Navon-Venezia, et al. First report on a hyperepidemic clone of KPC-3-producing Klebsiella pneumoniae in Israel genetically related to a strain causing outbreaks in the United States. Antimicrob

(56) References Cited

OTHER PUBLICATIONS

Agents Chemother. 2009;53(2):818-20. Epub Nov. 26, 2008. doi:10.1128/AAC.00987-08. PubMed PMID: 19029323; PubMed Central PMCID: PMC2630632.
Woodford, et al. Outbreak of Klebsiella pneumoniae producing a new carbapenem-hydrolyzing class A beta-lactamase, KPC-3, in a New York Medical Center. Antimicrob Agents Chemother. 2004;48(12):4793-9. Epub Nov. 25, 2004. doi: 48/12/4793 [pii] 10.1128/AAC.48.12.4793-4799.2004. PubMed PMID: 15561858; PubMed Central PMCID: PMC529220.
Snitkin, et al. Tracking a hospital outbreak of carbapenem-resistant Klebsiella pneumoniae with whole-genome sequencing. Science translational medicine. 2012;4(148):148ra16. doi: 10.1126/scitranslmed.3004129. PubMed PMID: 22914622; PubMed Central PMCID: PMC3521604.
Huntington P, Coatsworth N, Hardiman R, Hudson B, Kotsiou G, Fernandes C, editors. Klebsiella pneumoniae carbapenemase in Australia: detection of a KPC-producing clinical isolate at a Sydney hospital. The Australian Society for Microbiology 2011 Annual Conference; 2011; Hobart, Tasmania, Australia: The Australian Society for Microbiology 2011 Annual Conference.
Osterblad, et al. First isolations of KPC-2-carrying ST258 Klebsiella pneumoniae strains in Finland, June and Aug. 2009. Euro surveillance : bulletin Europeen sur les maladies transmissibles = European communicable disease bulletin. 2009;14(40). PubMed PMID: 19822122.
Hammerum, et al. Detection of the first two Klebsiella pneumoniae isolates with sequence type 258 producing KPC-2 carbapenemase in Denmark. Letters to the Editor/ Int J Antimicrob Agents. 2010;35(6):610-2. doi: 10.1016/j.jantimicag.2010.01.024. PubMed PMID: 20206479.
Giani, et al. Emergence in Italy of Klebsiella pneumoniae sequence type 258 producing KPC-3 Carbapenemase. J Clin Microbiol. 2009;47(11):3793-4. doi: 10.1128/JCM.01773-09. PubMed PMID: 19759220; PubMed Central PMCID: PMC2772625.
Cuzon, et al. Functional characterization of Tn4401, a Tn3-based transposon involved in blaKPC gene mobilization. Antimicrob Agents Chemother. 2011;55(11):5370-3. Epub Aug. 17, 2011. doi: AAC.05202-11 [pii] 10.1128/AAC.05202-11. PubMed PMID: 21844325; PubMed Central PMCID: PMC3195030.
Naas, et al. Role of ISKpn7 and deletions in blaKPC gene expression. Antimicrob Agents Chemother. 2012. Epub Jun. 27, 2012. doi: AAC.00334-12 [pii] 10.1128/AAC.00334-12. PubMed PMID: 22733068.
Endimiani, et al. Characterization of blaKPC-containing Klebsiella pneumoniae isolates detected in different institutions in the Eastern USA. J Antimicrob Chemother. 2009;63(3):427-37. Epub Jan. 22, 2009. doi: 10.1093/jac/dkn547. PubMed PMID: 19155227; PubMed Central PMCID: PMC2640158.
Gomez, et al. Clonal dissemination of Klebsiella pneumoniae ST258 harbouring KPC-2 in Argentina. Clin Microbiol Infect. 2011;17(10):1520-4. doi: 10.1111/j.1469-0691.2011.03600x. PubMed PMID: 21851480.
Garcia-Fernandez, et al. Klebsiella pneumoniae ST258 producing KPC-3 identified in Italy carries novel plasmids and OmpK36/OmpK35 porin variants. Antimicrob Agents Chemother. 2012. Epub Jan. 19, 2012. doi: AAC.05308-11 [pii] 10.1128/AAC.05308-11. PubMed PMID:22252815.
Leavitt, et al. Complete nucleotide sequence of KPC-3-encoding plasmid pKpQIL in the epidemic Klebsiella pneumoniae sequence type 258. Antimicrob Agents Chemother. 2010;54(10):4493-6. Epub Aug. 11, 2010. doi: AAC.00175-10 [pii] 10.1128/AAC.00175-10. PubMed PMID: 20696875; PubMed Central PMCID: PMC2944570.
Chen, et al. Comparative Genomic Analysis of KPC-Encoding pKpQIL-Like Plasmids and Their Distribution in New Jersey and New York Hospitals. Antimicrob Agents Chemother. 2014;58(5):2871-7. doi: 10.1128/AAC.00120-14. PubMed PMID: 24614371.
Adler, et al. A Swordless Knight: the epidemiology and molecular characteristics of the blaKPC-negative sequence-type 258 Klebsiella pneumoniae clone. J Clin Microbiol. 2012. Epub Jul. 21, 2012. doi: JCM.00987-12 [pii] 10.1128/JCM.00987-12. PubMed PMID: 22814467.
Frasson, et al. Antimicrobial treatment and containment measures for an extremely drug-resistant Klebsiella pneumoniae ST101 isolate carrying pKPN101-IT, a novel fully sequenced bla(KPC-2) plasmid. J Clin Microbiol. 2012;50(11)3768-72. Epub Sep. 14, 2012. doi:10.1128/JCM.01892-12 JCM.01892-12 [pii]. PubMed PMID: 22972824; PubMed Central PMCID: PMC3486238.
Mataseje, et al. Plasmid comparison and molecular analysis of Klebsiella pneumoniae harbouring bla(KPC) from New York City and Toronto. J Antimicrob Chemother. 2011;66(6):1273-7. Epub Mar. 17, 2011. doi: dkr092 [pii] 10.1093/ac/dkr092. PubMedPMID: 21406433.
Jiang, et al. Complete nucleotide sequence of Klebsiella pneumoniae multidrug resistance plasmid pKP048, carrying blaKPC-2, blaDHA-1, qnrB4, and armA. Antimicrob Agents Chemother. 2010;54(9):3967-9. Epub Jun. 16, 2010. doi: AAC.00137-10 [pii] 10.1128/AAC.00137-10. PubMed PMID: 20547789; PubMed Central PMCID: PMC2934982.
Almeida, et al. *Escherichia coli* ST502 and Klebsiella pneumoniae ST11 sharing an IncW plasmid harbouring the bla(KPC-2) gene in an Intensive Care Unit patient. Letters to the Editor / Int J Antimicrob Agents. 2012;40(4):374-6. Epub Jul. 24, 2012. doi: 10.1016/j.ijantimicag.2012.05.022. PubMed PMID: 22817916.
Lery, et al. Comparative analysis of Klebsiella pneumoniae genomes identifies a phospholipase D family protein as a novel virulence factor. BMC Biol. 2014;12:41. doi: 10.1186/1741-7007-12-41. PubMed PMID: 24885329; PubMed Central PMCID: PMC4068068.
Perera, et al. Molecular mechanisms of ligand-mediated attenuation of DNA binding by MarR family transcriptional regulators. Journal of molecular cell biology. 2010;2(5):243-54. doi: 10.1093/jmcb/mjq021. PubMed PMID: 20716550.
Grkovic, et al. Regulation of bacterial drug export systems. Microbiology and molecular biology reviews : MMBR. 2002;66(4):671-701, table of contents. PubMed PMID: 12456787; PubMed Central PMCID: PMC134658.
Li, et al. The challenge of efflux-mediated antibiotic resistance in Gram-negative bacteria. Clin Microbiol Rev. 2015;28(2):337-418. doi:10.1128/CMR.00117-14. PubMed PMID: 25788514.
Hao, et al. The multiple antibiotic resistance regulator MarR is a copper sensor in *Escherichia coli*. Nature chemical biology. 2014;10(1):21-8. doi: 10.1038/nchembio.1380. PubMed PMID: 24185215.
Wang, et al. Genetic characterisation of clinical Klebsiella pneumoniae isolates with reduced susceptibility to tigecycline: Role of the global regulator RamA and its local repressor RamR. Int J Antimicrob Agents. 2015. doi: 10.1016/j.ijantimicag.2014.12.022. PubMed PMID: 25681067.
De Majumdar, et al. Elucidation of the RamA Regulon in Klebsiella pneumoniae Reveals a Role in LPS Regulation. PLoS pathogens. 2015;11(1):e1004627. doi:10.1371/journal.ppat.1004627. PubMed PMID: 25633080; PubMed Central PMCID: PMC4310594.
Zhong, et al. First emergence of acrAB and oqxAB mediated tigecycline resistance in clinical isolates of Klebsiella pneumoniae pre-dating the use of tigecycline in a Chinese hospital. PLoS One. 2014;9(12):e115185. doi: 10.1371/journal.pone.0115185. PubMed PMID: 25503276; PubMed Central PMCID: PMC4264890.
Hansen, et al. Plasmid-encoded multidrug efflux pump conferring resistance to olaquindox in *Escherichia coli*. Antimicrob Agents Chemother. 2004;48(9):3332-7. doi: 10.1128/AAC.48.9.3332-3337.2004. PubMed PMID: 15328093; PubMed Central PMCID: PMC514751.
Perez, et al. OqxAB, a quinolone and olaquindox efflux pump, is widely distributed among multidrug-resistant Klebsiella pneumoniae isolates of human origin. Antimicrob Agents Chemother. 2013;57(9):4602-3. doi: 10.1128/AAC.00725-13. PubMed PMID: 23817374; PubMed Central PMCID: PMC3754307.
Bialek-Davenet, et al. Differential contribution of AcrAB and OqxAB efflux pumps to multidrug resistance and virulence in

(56) References Cited

OTHER PUBLICATIONS

Klebsiella pneumoniae. J Antimicrob Chemother. 2015;70(1):81-8. doi: 10.1093/jac/dku340. PubMed PMID: 25193085.

* cited by examiner

SEQUENCE LISTING

```
<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: oligonucleotide

<400> SEQUENCE: 1

atggtggtgc gccagtg                                                    17


<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2

gctgaccgag acgttgtc                                                   18


<210> SEQ ID NO 3
<211> LENGTH: 17
<212> TYPE: DNA
<213> ORGANISM: Artificial Sequence
<220> FEATURE:
<223> OTHER INFORMATION: Oligonucleotide

<400> SEQUENCE: 3

cattattgac ttcgcta                                                    17


<210> SEQ ID NO 4
```

-continued

```
<211> LENGTH: 16
<212> TYPE: DNA
<213> ORGANISM: Artificial Sequence
<220> FEATURE:
<223> OTHER INFORMATION: Oligonucleotide

<400> SEQUENCE: 4

ccattattga ctccgc                                                    16


<210> SEQ ID NO 5
<211> LENGTH: 15
<212> TYPE: DNA
<213> ORGANISM: Artificial Sequence
<220> FEATURE:
<223> OTHER INFORMATION: Oligonucleotide

<400> SEQUENCE: 5

acggcaggcg atttg                                                     15


<210> SEQ ID NO 6
<211> LENGTH: 15
<212> TYPE: DNA
<213> ORGANISM: Artificial Sequence
<220> FEATURE:
<223> OTHER INFORMATION: Oligonucleotide

<400> SEQUENCE: 6

agctgcgtga tcgag                                                     15


<210> SEQ ID NO 7
<211> LENGTH: 15
<212> TYPE: DNA
<213> ORGANISM: Artificial Sequence
<220> FEATURE:
<223> OTHER INFORMATION: Oligonucleotide

<400> SEQUENCE: 7

cgctgaaggt agcga                                                     15


<210> SEQ ID NO 8
<211> LENGTH: 15
<212> TYPE: DNA
<213> ORGANISM: Artificial Sequence
<220> FEATURE:
<223> OTHER INFORMATION: Oligonucleotide

<400> SEQUENCE: 8

ctgaaggtgg cgaga                                                     15
```

METHODS AND KITS TO IDENTIFY KLEBSIELLA STRAINS

CROSS REFERENCE TO RELATED APPLICATIONS

The present application claims the benefit of U.S. Provisional Application No. 62/195,206 filed Jul. 21, 2015, the contents of which are incorporated herein by reference for any purpose.

STATEMENT REGARDING FEDERALLY SPONSORED RESEARCH

This invention was made with government support under A1090782 awarded by the National Institutes of Health. The government has certain rights in this invention.

FIELD OF INVENTION

The present invention is generally related to methods of identifying pathogenic microorganisms and specifically related to methods and kits of detecting clinically relevant *Klebsiella* species.

BACKGROUND OF THE INVENTION

Enterobacteriaceae are a common cause of healthcare-associated bacterial infections, including pneumonia, meningitis, sepsis, and other life threatening illness, especially among patients with underlying medical conditions. The recent rise of carbapenem-resistant Enterobacteriaceae (CRE) has left clinicians with limited antimicrobial treatment options for these infections, and has been declared an immediate public health threat that requires urgent and aggressive action by the Centers for Disease Control and Prevention [1]. *Klebsiella pneumoniae* carbapenemase (KPC)-producing *K. pneumoniae* are now one of the most widely disseminated CRE pathogens, and are associated with high morbidity and mortality rates [2, 3]. Since their initial identification in 2001 [1], KPC-producing *K. pneumoniae* have emerged throughout the United States (currently identified in 47 states; CDC unpublished data) and the world, spanning five continents that also include South America, Eurasia, Africa and Australia [5-7].

The rapid, widespread dissemination of KPC-producing *K. pneumoniae* is largely attributed to the clonal expansion of a single dominant strain, sequence type (ST) 258 as defined by multilocus sequence typing or MLST, currently circulating in over 20 countries [6]. ST258 is a member of the recently designated clonal group (CG) 258 [8], which comprises several other sequence types linked to outbreaks, suggesting that these strains may share genetic features that predispose them to pathogenicity or increased transmissibility. Unlike ST258, other CG258 strains are associated with a variety of carbapenemases including KPC, NDM, VIM, and OXA-48 [9-11]. The transmission of KPC-producing ST258 and other CG258 strains is frequently linked to patient travel or healthcare exposure in known endemic areas, such as the United States, Israel, and Greece [6, 12, 13]. Despite previous genomic analyses of ST258 [14-18], an explanation for its pathogenic success in the healthcare system remains unclear.

Large homologous recombination events frequently shape genomes to result in new emerging pathogens [19]. A sequence of these events has now been documented for CG258 and ST258. Gaiarsa and colleagues, using sequence from Italian isolates and the public database, discovered a putative recombination event that gave rise to CG258. Their evidence shows a donor related to *K. pneumoniae* ST1628 contributed ~1.3 Mbp to an ancestor of ST11 (CG258) sometime before 1985 [17]. Chen and colleagues used public genomic data to show the ST258 lineage resulted from a ~1.1 Mbp recombination event between ST11 and a strain related to a Brazilian ST442 isolate [20]. DeLeo and colleagues published a whole genome SNP-based phylogeny of ST258 from mostly the northeastern U.S., and concluded that ST258 comprises two distinct lineages which diverged after a homologous recombination event of ~215 kb that included the capsule polysaccharide synthesis (cps) locus [15]. Additionally, Wyres and colleagues documented several recombination events involving cps loci in CG258 [18].

Given these concerns and motivations, there is a demonstrated need in the art for a panel of real-time PCR assays, based on competitive probe methodology, for rapid and sensitive molecular detection of clinically relevant *Klebsiella pneumoniae* strains. Competitive probe assays, a form of allele-specific PCR (ASPCR), employs primers that are designed for SNP analysis.

BRIEF SUMMARY OF THE INVENTION

Some embodiments may provide a method of detecting carbapenem-resistant Enterobacteriaceae (e.g., *Klebsiella pneumoniae*) in a sample, the method comprising the steps of: (i) adding a first, a second, and a third oligonucleotide to a mixture comprising the sample, wherein the first, second, and third oligonucleotides added to the mixture include a sequence selected from the group consisting of SEQ ID NO: 1, SEQ ID NO: 2, SEQ ID NO: 3, and SEQ ID NO: 4; (ii) subjecting the mixture to conditions that allow nucleic acid amplification; and (iii) detecting the carbapenem-resistant Enterobacteriaceae in the sample on the basis of results of the nucleic acid amplification in the mixture. In some aspects, the results comprises a Ct value and the sample comprises an environmental sample and/or is derived from a subject (e.g., a sputum sample).

Embodiments may include a method of detecting a *Klebsiella pneumoniae* carbapenemase (KPC)-producing strain (e.g., strain ST258) in a sample, the method comprising the steps of: (i) adding a first, a second, and a third oligonucleotide to a first mixture comprising the sample, wherein the first, second, and third oligonucleotides added to the first mixture include a sequence selected from the group consisting of SEQ ID NO: 1, SEQ ID NO: 2, SEQ ID NO: 3, and SEQ ID NO: 4; (ii) adding a first, a second, and a third oligonucleotide to a second mixture comprising the sample, wherein the first, second, and third oligonucleotides added to the second mixture include a sequence selected from the group consisting of SEQ ID NO: 1, SEQ ID NO: 2, SEQ ID NO: 3, and SEQ ID NO: 4; (iii) subjecting the first and second mixtures to conditions that allow nucleic acid amplification; and (iv) detecting the KPC-producing isolate in the sample on the basis of results of the nucleic acid amplification in the first and second mixtures. The method may also include wherein the first, second, and third oligonucleotides added to the first mixture include a sequence selected from the group consisting of SEQ ID NO: 1, SEQ ID NO: 2, and SEQ ID NO: 3 and/or wherein the first, second, and third oligonucleotides added to the second mixture include a sequence selected from the group consisting of SEQ ID NO: 1, SEQ ID NO: 2, and SEQ ID NO: 4. In some aspects, the result comprises a Ct value and wherein if the ST258 isolate is present in the sample, a Ct value in the first mixture will be lower than a Ct value in the second mixture. In some aspects, the sample comprises an environmental sample and/or is derived from a subject (e.g., a sputum sample).

Embodiments may provide a method of detecting a *Klebsiella pneumoniae* ST258 strain in a sample, the method comprising the steps of: (i) adding a first, a second, and a third oligonucleotide to a first mixture comprising the sample, wherein the first, second, and third oligonucleotides added to the first mixture include a sequence selected from the group consisting of SEQ ID NO: 1, SEQ ID NO: 2, SEQ ID NO: 3, and SEQ ID NO: 4; (ii) adding a first, a second, and a third oligonucleotide to a second mixture comprising the sample, wherein the first, second, and third oligonucleotides added to the second mixture include a sequence selected from the group consisting of SEQ ID NO: 1, SEQ ID NO: 2, SEQ ID NO: 3, and SEQ ID NO: 4; (iii) subjecting the first and second mixtures to conditions that allow nucleic acid amplification; and (iv) detecting the *Klebsiella pneumoniae* ST258 strain in the sample on the basis of a difference in amplification efficiency of the nucleic acid amplification in the first and second mixtures. In some aspects, the first, second, and third oligonucleotides added to the first mixture include a sequence selected from the group consisting of SEQ ID NO: 1, SEQ ID NO: 2, and SEQ ID NO: 3 and/or the first, second, and third oligonucleotides added to the second mixture include a sequence selected from the group consisting of SEQ ID NO: 1, SEQ ID NO: 2, and SEQ ID NO: 4. In some aspects, if the *Klebsiella pneumoniae* ST258 strain is detected in the subject the method further comprises of the step of administering to the subject a therapeutically effective amount of an antibiotic to which the *Klebsiella pneumoniae* ST258 strain is sensitive.

BRIEF DESCRIPTION OF THE DRAWINGS

(FIG. 2A) A maximum parsimony phylogeny based on 1,440 core genome SNPs in 138 CG258 isolates using NJST258_1 with the 1.06 Mbp region of recombination [20] masked as a reference reduces the genomic distance between ST258 and the rest of CG258. The consistency index of the maximum parsimony phylogeny is 0.95, indicating most SNPs in the core are vertically transferred. (FIG. 2B) A maximum parsimony phylogeny based on 1,425 core genome SNPs in 102 ST258 isolates, using NJST258_1 with the 215 kb region of recombination [15] masked as a reference illustrate the clonal nature and evolutionary history of ST258. The consistency index is 0.96 for the ST258 maximum parsimony phylogeny, indicating most SNPs in the core are vertically transferred.

DETAILED DESCRIPTION

Figure 1:
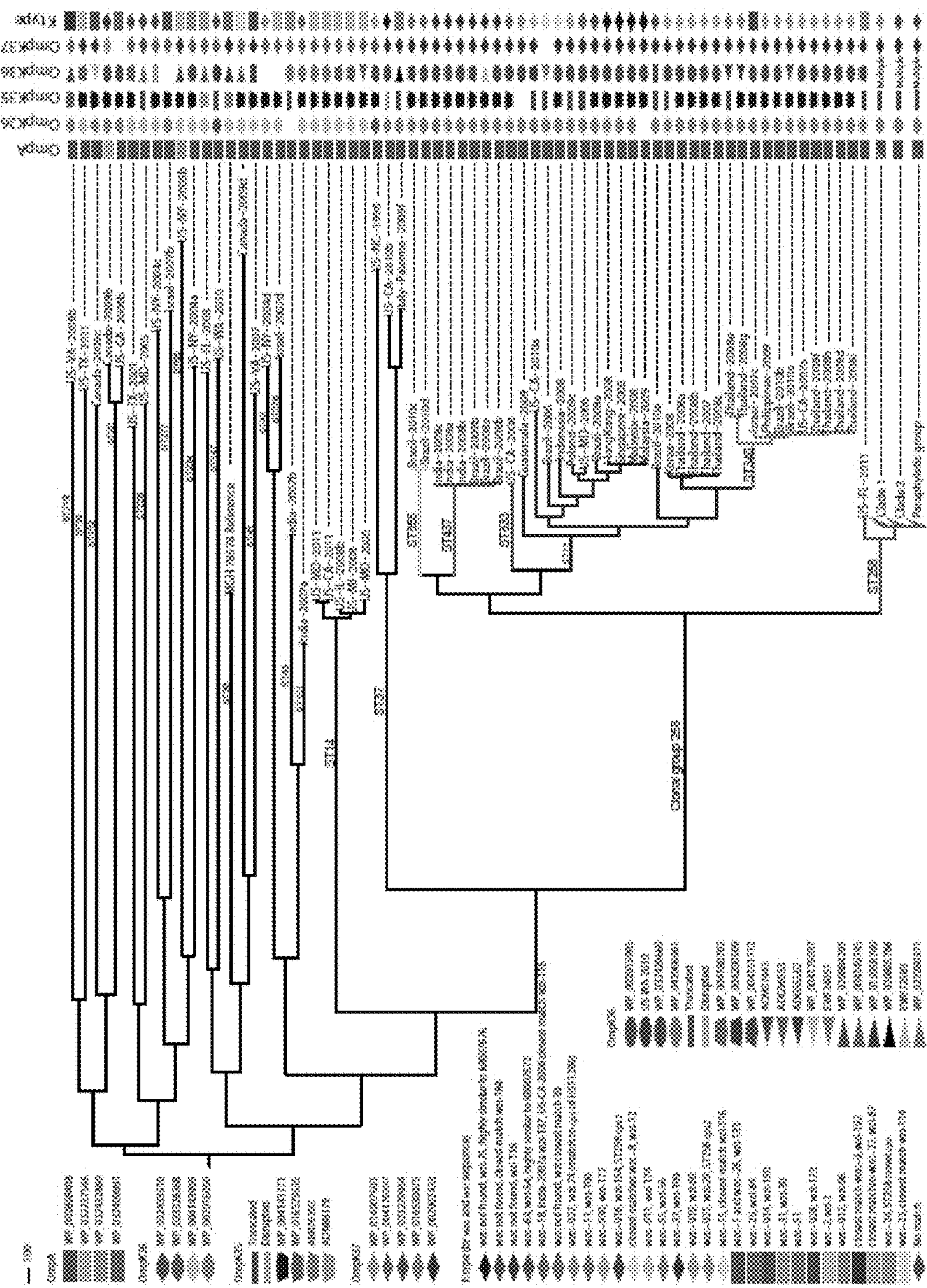
FIG. 1. Genetic diversity of healthcare-associated *K. pneumoniae*. A maximum parsimony phylogeny based on 49,094 core genome SNPs in 165 *K. pneumoniae* isolates and the reference genome MGH 78578 illustrate the diversity of *K. pneumoniae* pathogens. The consistency index of the phylogeny is 0.34, reflecting a high number of homoplasious SNPs and indicative of high levels of homologous recombination. (Non-homologous DNA is not analyzed, as it is not part of the core genome.) The main branches of the groups within ST258 are collapsed. In CG258, branches are colored by sequence type. Outer membrane protein sequence was matched by BLAST to a Genbank accession number, except in the case of OmpK36 where matches of high similarity were not always found, in which case the sample name was used as the identifier. The cps loci of all strains were characterized by the wzc and wzi sequences [76, 77] and full-length characterization where genome assemblies allowed.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Inventors are fully aware that they can be their own lexicographers if desired.

Herein disclosed are methods and kits that can be employed to detect one or more species of *Klebsiella* (e.g., *K. pneumoniae*). For example, some of the methods disclosed herein can be used to assess the presence of one or more strains of *K. pneumoniae*. For instance, some methods disclosed herein can be used to determine the presence of *K. pneumoniae* strain ST258. Moreover, in some aspects, the methods disclosed herein can be used to elucidate whether a sample comprises *K. pneumoniae* from clonal group (CG) 258, which may include strain ST258 in addition to strain *K. pneumoniae* carbapenemase (KPC)-producing *K. pneumoniae*, or strains containing NDM, VIM, and OXA-48.

Furthermore, in some embodiments, after determination of the presence of *K. pneumoniae*, including clonal groups and/or strains thereof, based upon the organism(s) contained in the sample, the method may further include treating the subject from which the sample originated with one or more pharmaceutical compositions comprising one or more antibiotics to which the *K. pneumoniae* is predicted to be at least partially sensitive. For example, in some embodiments, the subject can be treated with an antibiotic to which the *K. pneumoniae* is not resistant (i.e., not carbapenem). Moreover, in some aspects, one or more strains of *K. pneumoniae* may be resistant to one or more antibiotics that may be traditionally used to treat bacterial infections (e.g., Gram negative bacterial infections). For example, some strains of *K. pneumoniae* (e.g., ST258) may be resistant to treatment with carbapenem, fluoroquinolones, and aminoglycosides, among other antibiotics that are known to those of ordinary skill in the art. In some aspects, the subject from which the sample originated may be treated with an antibiotic analogous to a "last line of defense" (e.g., colistin), which may have one or more undesirable side effects. As such, those of skill in the art will find it beneficial to determine the strain and resistance capabilities of the *K. pneumoniae* strains.

Some embodiments of the invention may also provide methods of detecting/diagnosing a subject with an infection with one or more carbapenem-resistant Enterobacteriaceae. For example, in some embodiments, methods may include diagnosing a subject as having an infection with KPC or other strains of *K. pneumoniae* that may produce carbapenemase (i.e., an enzyme that may confer resistance to carbapenem. In some aspects, the method may further include treating the subject with one or more antibiotics to which the carbapenem-resistant Enterobacteriaceae are predicted to be sensitive (i.e., not carbpenem). In order to make these determinations, some aspects of the methods disclosed herein may rely on the assessment/determination of a status of one or more markers.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A reagent capable of binding to a nucleic acid sequence having less than 60% 70%, 80%, 90%, 95%, 99% or 100% identity to the identifying sequence may still be encompassed by the invention if it is still capable of binding to its complimentary sequence and/or facilitating nucleic acid amplification of a desired sequence. Although a nucleic acid sequence represented by the sequence of a single nucleic acid strand (e.g. the 5'→3' strand) the totality of reagents that bind to the sequence also includes all reagents capable of binding to the complementary strand (e.g the 3'→5' strand). If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence. Examples of molecules encompassed by a marker represented by a particular sequence or structure include point mutations, single nucleotide polymorphisms (SNPs), silent mutations, deletions, frameshift mutations, translocations, alternative splicing derivatives, differentially methylated sequences, truncations, soluble forms of cell membrane associated markers, and any other variation that results in a product that may be identified as the marker. The following nonlimiting examples are included for the purposes of clarifying this concept: If expression of a specific marker in a sample is assessed by PCR, and if the sample expresses an DNA sequence different from the sequence used to identify the specific marker by one or more nucleotides, but the marker may still be detected using PCR, then the specific marker encompasses the sequence present in the sample. A marker may also be represented by a protein sequence, which includes mutated and differentially modified protein sequences.

The invention may comprise methods of detecting one or more strains of *K. pneumoniae* in a sample. A sample may be derived from anywhere that fungus or any part of a fungal body may be found including soil, air, water, solid surfaces (whether natural or artificial,) culture media, foodstuffs, and any interfaces between or combinations of these elements. Additionally, a sample may be derived from a subject, such as a plant or animal, including humans. Samples derived from animals include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, urine, hair, or any other source in which a fungus, or any part of a fungus might be present. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may also include *K. pneumoniae* that has been previously isolated from one or more prior samples and grown in an isolated environment (e.g., a laboratory). Thereafter, one or more biomolecules (e.g., nucleic acids or protein) can be isolated from the *K. pneumoniae* for used in the methods disclosed herein.

Direct methods of detecting the presence of a marker include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, or any combination of these; allele specific ligation; comparative genomic hybridization; array based genotyping including SNP genotyping, or any other method that allows the detection of a particular nucleic acid sequence within a sample or enables the differentiation of one nucleic acid from another nucleic acid that differs from the first nucleic acid by one or more nucleotides. A sample may be suspected of including a nucleic acid from a fungus of interest. A subject may be any organism that may be infected by a virus including bacteria, plants, animals, chordates, mammals, humans, insects, endangered species, or any other organism of agricultural, environmental, or other significance.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a pyrophosphate upon nucleotide incorporation. An ATP sulfurylase enzyme converts pyrophosphate into ATP which in turn catalyzes the conversion of luciferin to oxyluciferin which results in the generation of visible light that is then detected by a camera.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Indirect methods of detecting a marker generally involve assessing the expression of material created from a genomic DNA template such as a RNA or protein molecule. Such expression may be assessed by any of a number of methods used currently in the art and yet to be developed. Examples include any nucleic acid detection method including the following non-limiting examples, microarray RNA analysis, RNA in situ hybridization, RNAse protection assay, Northern blot, reverse transcription PCR, and quantitative reverse transcription PCR. Other examples include any process of detecting expression that uses an antibody including the following non-limiting examples, flow cytometry, immunohistochemistry, ELISA, Western blot, Northwestern blot, and immunoaffinity chromatography. Antibodies may be monoclonal, polyclonal, or any antibody fragment including an Fab, $F(ab)_2$, Fv, scFv, phage display antibody, peptibody, multispecific ligand, or any other reagent with specific binding to a target. Other methods of assessing protein expression include the following non-limiting examples: HPLC, mass spectrometry, protein microarray analysis, PAGE analysis, isoelectric focusing, 2-D gel electrophoresis, and enzymatic assays.

A reagent may be any substance that facilitates any method of detecting a marker. Examples of reagents include nucleic acids such as oligonucleotide probes, nucleic acid mixtures, or full length nucleic acids; proteins such as antibodies, natural ligands, or enzymes; or small molecule compounds in or out of solution such as drugs, buffers, vitamins, or any other artificial or naturally occurring compound that may facilitate the detection of a marker. A reagent may be capable of specific binding to the marker such as a nucleic acid probe or antibody with specificity for the marker.

A reagent may be added to a sample by any of a number of methods including manual methods, mechanical methods, or any combination thereof. The presence of the marker may be signified by any of a number of methods including amplification of a specific nucleic acid sequence, sequencing of a native or amplified nucleic acid, or the detection of a label either bound to or released as a result of the detection of the marker. Addition of a reagent capable of specifically binding a marker to a sample also encompasses addition of the reagent to a sample in which the marker to which the nucleic acid has specificity is absent.

In some aspects of the invention, the presence of a marker may be established by binding to a microarray such as a DNA chip. Examples of DNA chips include chips in which a number of single stranded oligonucleotide probes are affixed to a solid substrate such as silicon glass. Oligonucleotides capable of binding to a marker are capable of hybridizing to all or part of the marker to the exclusion of sequences that differ from those included within the marker by one or more nucleotides. The number of nucleotide differences that may be tolerated are dependent upon the hybridization conditions. Labeled sample DNA is hybridized to the oligonucleotides and detection of the label is correlated with binding of the sample and consequently the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A reagent may be affixed to a substrate. In other aspects of the invention, a sample may be affixed to the substrate and made available to a reagent in solution. A reagent or sample may be covalently bound to the substrate or it may be bound by some non-covalent interaction including electrostatic, hydrophobic, hydrogen bonding, Van Der Waals, magnetic, or any other interaction by which a reagent capable of specific binding to a marker such as an oligonucleotide probe may be attached to a substrate while maintaining its ability to recognize the marker to which it has specificity. A substrate may be any solid or semi-solid material onto which a probe may be affixed, attached or printed, either singly or in the presence of one or more additional probes or samples as is exemplified in a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A reagent may include a label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include but are not limited to: fluorescein, biotin, digoxigenin, alkaline phosphatase, biotin, streptavidin, $^{3}H$, $^{14}C$, $_{32}P$, $^{35}S$, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of such dyes include but are not limited to: FAM, dR110, 5-FAM, 6FAM, dR6G, JOE, HEX, VIC, TET, dTAMRA, TAMRA, NED, dROX, PET, BHQ+, Gold540, and LIZ.

A nucleotide is an individual deoxyribonucleotide or ribonucleotide base. Examples of nucleotides include but are not limited to: adenine, thymine, guanine, cytosine, and uracil, which may be abbreviated as A, T, G, C. or U in representations of oligonucleotide or polynucleotide sequence. Any molecule of two or more nucleotide bases, whether DNA or RNA, may be termed a nucleic acid.

A nucleic acid reagent may be affixed to a solid substrate. Alternatively, the sample may be affixed to a solid substrate and the oligonucleotide placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non-covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi-solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

Nucleic acid amplification may be performed using nucleic acids from any source. In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA,) amplification with Qβ replicase, whole genome amplification with enzymes such as φ29, whole genome PCR, in vitro transcription with Klenow or any other RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that may be based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. RNA may be detected by PCR analysis by creating a DNA template from RNA through a reverse transcriptase enzyme. In some aspects of the invention, the marker may be detected by quantitative PCR analysis, which may be performed using a kit containing components that facilitate genotyping analysis. Genotyping analysis may be performed using a probe that is capable of hybridizing to a nucleic acid sequence of interest.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

Oligonucleotide synthesis is the chemical synthesis of oligonucleotides with a defined chemical structure and/or nucleic acid sequence by any method now known in the art or yet to be disclosed. Oligonucleotide synthesis may be carried out by the addition of nucleotide residues to the 5'-terminus of a growing chain. Elements of oligonucleotide synthesis include: De-blocking: A DMT group is removed with a solution of an acid, such as TCA or Dichloroacetic acid (DCA), in an inert solvent (dichloromethane or toluene) and washed out, resulting in a free 5' hydroxyl group on the first base. Coupling: A nucleoside phosphoramidite (or a mixture of several phosphoramidites) is activated by an acidic azole catalyst, tetrazole, 2-ethylthiotetrazole, 2-bezylthiotetrazole, 4,5-dicyanoimidazole, or a number of similar compounds. This mixture is brought in contact with the starting solid support (first coupling) or oligonucleotide precursor (following couplings) whose 5'-hydroxy group reacts with the activated phosphoramidite moiety of the incoming nucleoside phosphoramidite to form a phosphite triester linkage. The phosphoramidite coupling may be carried out in anhydrous acetonitrile. Unbound reagents and by-products may be removed by washing. Capping: A small percentage of the solid support-bound 5'-OH groups (0.1 to 1%) remain unreacted and should be permanently blocked from further chain elongation to prevent the formation of oligonucleotides with an internal base deletion commonly referred to as (n−1) shortmers. This is done by acetylation of the unreacted 5'-hydroxy groups using a mixture of acetic anhydride and 1-methylimidazole as a catalyst. Excess reagents are removed by washing. Oxidation: The newly formed tricoordinated phosphite triester linkage is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. This step can be substituted with a sulfurization step to obtain oligonucleotide phosphorothioates. In the latter case, the sulfurization step is carried out prior to capping. Upon the completion of the chain assembly, the product may be released from the solid phase to solution, deprotected, and collected. Products may be isolated by HPLC to obtain the desired oligonucleotides in high purity.

Some aspects of the invention include the use of one or more oligonucleotides. For example, the oligonucleotides can include the following sequences: ATGGTGGTGCGCCAGTG (SEQ ID NO: 1), GCTGACCGAGACGTTGTC (SEQ ID NO: 2), CATTATTGACTTCGCTA (SEQ ID NO: 3), CCATTATTGACTCCGC (SEQ ID NO: 4), ACGGCAGGCGATTTG (SEQ ID NO: 5), AGCTGCGTGATCGAG (SEQ ID NO: 6), CGCTGAAGGTAGCGA (SEQ ID NO: 7), and/or CTGAAGGTGGCGAGA (SEQ ID NO: 8). As described in greater detail herein, these one or more mixtures of these oligonucleotides can be used in detecting one or more strains or clonal groups of *K. pneumoniae*.

Kits that facilitate methods of detecting a marker may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication of a result of the use of the kit that signifies a particular characteristic. An indication includes any guide to a result that would signal the presence or absence of any characteristic that the kit is configured to predict. For example, the indication may be expressed numerically, expressed as a color or density of a color, expressed as an intensity of a band, derived from a standard curve, or expressed in comparison to a control. The indication may be communicated through the use of a writing. A writing may be any communication of the result in a tangible medium of expression. The writing may be contained physically in or on the kit (on a piece of paper for example), posted on the Internet, mailed to the user separately from the kit, or embedded in a software package. The writing may be in any medium that communicates how the result may be used to predict the cellular or physiological characteristic that the kit is intended to predict, such as a printed document, a photograph, sound, color, or any combination thereof.

Some embodiments of the invention may also provide methods of providing helpful epidemiological information. For example, some strains of *K. pneumoniae* (e.g., ST258) may easily and rapidly spread through certain care facilities (e.g., nursing homes, hospitals, long-term care institutions, etc.). As such, it would be beneficial to make a determination about the strain and origin of an infectious *K. pneumoniae* strain when planning an outbreak response in one of these care facilities. For example, it would be helpful in planning an outbreak response to know whether a particular subject is infected with the outbreak strain (e.g., ST258) or a strain not tied to the outbreak (e.g., a non-ST258 strain).

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

EXAMPLES

Materials and Methods

Strain Collection

This work's *K. pneumoniae* isolated in the United States (n=72) were selected from the CDC's collection, which primarily comprises isolates submitted for reference testing or as part of an outbreak investigation in which the CDC was involved. Selection criteria were based on PFGE profiles, MLST sequence types when available, geography, year of isolation, and KPC status. U.S. isolates were selected with a focus on ST258, followed by other CG258 and non-CG258 isolates. Isolates from other countries (n=95) were generously donated upon a request to various countries with recent reports of KPC-producing ST258 or CG258 strains.

Sequencing, MLST, and SNP Detection

Genome libraries were prepared with a 500 base pair insert size using a KAPA Library Preparation Kit with Standard PCR Library Amplification (Kapa Biosystems, Wilmington, Mass.) and sequenced on a 101 bp read, paired-end Illumina GAIIx run. SRST2 [65] was used to determine multilocus sequence types. NASP, a pipeline developed by TGen North, was used to detect SNPs. In brief, reads were aligned to the finished *K. pneumoniae* genomes MGH 78578 (GenBank accession no. CP000647) or the ST258 reference genome NJST258_1 (GenBank CP006923) using Novoalign (Novocraft.com) and SNPs called with GATK [66]. Data filtered out included SNP loci with less than 10× coverage or with less than 90% consensus in any one sample, regions duplicated in the reference genome as identified by Nucmer, and SNP loci that were not present in all genomes in the dataset. The results were output in a SNP matrix from a core genome common to all isolates in the analysis. Core genome size is expressed as the size of the reference genome (or percentage of the total reference genome size) excluding repeated regions and covered by reads at 10× or higher depth by all samples, or the length of the DNA that all samples in a given set have in common after filtering based on the above criteria. Read data were deposited in the NCBI SRA database under BioProject ID PRJNA252957.

Phyloaenetic Analysis

Phylogenetic trees were generated from the SNP matrices using the maximum parsimony method with 1000 bootstraps in MEGA 5.2 [67] [68] and subsequently plotted by means of ITOL v2 [69]. The genome of a *K. oxytoca* isolate (GenBank accession no. CP003218) was used as the outgroup to root an initial *K. pneumoniae* tree. The isolates with the basal-most branch, or the isolates with the branch closest to the outgroup, was used as the outgroup to root the following tree without *K. oxytoca*. All subsequent trees to analyze a progressively smaller number of isolates used the isolates with the basal-most branch from the previous tree as the root.

Bayesian evolutionary analysis was performed in BEAST v1.7.4 [70] using the SNP matrix generated by NASP to compute evolutionary rates and divergence times using the GTR model of nucleotide substitution and an uncorrelated log normal relaxed clock. A tree prior of exponential growth was used along with a random starting tree and an exponential growth rate set to random walk. Isolates were dated based on the year of isolation and were run with 50 million generations and a burn-in phase of 5 million. Three independent Markov Chain Monte Carlo analyses were completed and combined in order for all parameters' effective sample size values to be larger than 500.

Targeted Genome Analysis

Plasmid incompatibility groups were detected in silico by uploading read data to PlasmidFinder [71]. Known horizontally transferred antibiotic resistance genes were detected with SRST2 [65, 72]. Selected genes were also aligned to a reference gene with SeqMan NGen (DNASTAR, Madison, Wis.) to confirm their presence and type in read data. Reads were assembled using SPAdes Genome Assembler [73] after trimming Illumina adaptors with Trimmomatic [74]. Porin sequences were analyzed using SSTAR and Geneious [75], and cps loci and Tn4401 were characterized using Geneious [75] and SeqMan NGen (DNASTAR, Madison, Wis.). Capsule types were assigned using the wzc and wzi sequence databases in BIGSdb ([76, 77].

SNP Assays

Real-time PCR assays targeting the SNPs specific to ST258 and CG258 were designed with Biosearch Technologies' RealTimeDesign™ software (Biosearch Technologies, Petaluma, Calif.). Assays were run in 10 uL reactions on the 7900HT instrument (Life Technologies, Carlsbad, Calif.) with 1× PerfeCTa qPCR FastMix II (Quanta Biosciences, Gaithersburg, Md.), 600 nM forward and reverse primers, 200 nM each probe, and 1 μL DNA template (approximately 0.5 ng). Thermal conditions included denaturation for 4 min at 95° C. followed by 40 cycles of 15 s at 95° C. and 1 min at 60° C.

Results

Genomics of *K. pneumoniae*

The inventors' whole genome sequence analyses are based on SNPs, which are inherently stable, that fall in the core genome, or only the regions of the genome homologous to all isolates in the sample set (see details in Materials and Methods). Whole genome analysis of the 167 diverse isolates resulted in a core genome size of 2.2 Mbp. After two clear outliers were removed (a ST334 and a novel sequence type that were more than 37,000 SNPs from their closest neighbor), the core was still small at 2.4 Mbp (Table 1) compared to the known *K. pneumoniae* chromosome size of 5.1 to 5.4 Mbp (from publicly available genomes of clinical isolates). This signifies a lack of genomic overlap among the isolates, likely due to a large number of genes acquired through horizontal gene transfer (HGT) and non-homologous recombination. These calculations show, even with a limited number of isolates outside CG258, that *K. pneumoniae* is a very diverse species; the average pairwise SNP distance between sequence types is 8,490. The maximum parsimony reconstruction of the phylogeny using the SNP data support this, illustrating diversity even in the homologous regions of the genomes with long branches between isolates (FIG. 1).

The inventors' analyses provide the resolution to infer evolutionary history and exemplify the limitations of relational inferences from the traditional seven-locus MLST scheme. The adoption of the scgMLST scheme and clonal group nomenclature proposed by Bialek-Davenet et al. [8] address these limitations, however a full conversion from MLST-derived "sequence types" has yet to be proposed. Hundreds of SNPs separate ST258 from most MLST single locus variants (SLVs); the average pairwise SNP distance between ST258 isolates and those of the rest of the clonal group is 304 SNPs. Long branches separating isolates of the same sequence type or within the same clonal group, for example in ST37 and within CG258, often signify homologous recombination events like those documented by Gaiarsa, Chen, and DeLeo [15, 17, 20]. In contrast, ST512 and ST1199 are point mutation SLVs of ST258 and are clearly part of the ST258 lineage, and for ease of reading, are referred to as ST258 throughout. ST258 is a closely related group (average pairwise SNP distance of 13) within its diverse ancestral group (average pairwise SNP distance of the remaining isolates in CG258 is 214). This is evidence that ST258 is a recent emergence from the ancestral CG258 clade (FIG. 1).

isolates are paraphyletic with respect to Clades 1 and 2. Within the context of ST258's genetic relationships with other *K. pneumoniae*, the data illustrate that ST258 isolates are of a single clonal lineage derived from a recent common ancestor.

TABLE 1

Results of mapping Illumina sequencing reads from *K. pneumoniae* isolates to relevant reference genomes. For further definition of the calculations see Materials and Methods.

| Sample set | No. isolates | Reference genome (genome size) | Total no. SNPs | No. SNPs parsimony informative | Total breadth of reference genome coverage (Core genome size) | Breadth of reference genome coverage all samples | Maximum parsimony consistency index | Illustr. |
|---|---|---|---|---|---|---|---|---|
| *K. pneumoniae* this study | 167 | MGH 78578 (5.32 Mbp) | 163,711 | 54,853 | 40.7% (2.16 Mbp) | >70.8% | 0.53 | Data not shown |
| *K. pneumoniae* 2 outliers pruned | 165 | MGH 78578 (5.32 Mbp) | 49,094 | 24,735 | 44.6% (2.37 Mbp) | >70.8% | 0.34 | FIG. 1 |
| CG258 | 138 | NJST258_1 ~1.1 Mbp masked (4.2 Mbp) | 7,256 | 4,626 | 50.0% (2.1 Mbp) | >77.6% | 0.60 | FIG. 2A |
| ST258* | 102 | NJST258_1 ~215 kb masked (5.05 Mbp) | 1,425 | 307 | 75.5% (3.82 Mbp) | >93.1% | 0.96 | FIGS. 2B and 3 |
| ST258 from this study* and SRA Study SRP036874** | 185 | NJST258_1 ~210 kb masked (5.05 Mbp) | 2,282 | 582 | 72.3% (3.65 Mbp) | >93.1% | 0.96 | S1 FIG. |

*Including ST512 and ST1199, both point mutations SLVs of ST258

**Including ST379, ST512, and ST418, all SLVs of ST258 [15]

In order to illustrate the evolutionary history of all members of CG258, the inventors masked the large regions of recombination identified in previous studies from the finished chromosome of the ST258 isolate NJST258_1 [15, 20] to filter non-phylogenetically informative SNP loci. Phylogenies of closely related isolates or defined by few SNPs can be heavily influenced by SNPs in recombinant regions leading to false inferences of evolutionary history. Reads from the 137 isolates in CG258 were mapped to NJST258_1 and the 1.06 Mbp recombinant region [20] was masked, resulting in a reference genome of 4.2 Mbp. A significant reduction in the pairwise SNP distance comparison between ST258 and the rest of CG258 resulted; an average of 62 SNPs separate the isolates from the two groups (compared to 304 stated above). The phylogeny from these data illustrates that ST11 is a paraphyletic group with respect to ST437, ST340, and ST258, and only four SNPs distinguish the ST258 lineage from its clonal group (FIG. 2A). The core genome in this analysis is 50% of the 4.2 Mbp reference genome, or 2.1 Mbp (Table 1), implying that there are many regions of non-homologous recombination in this sample set.

Figure 2:
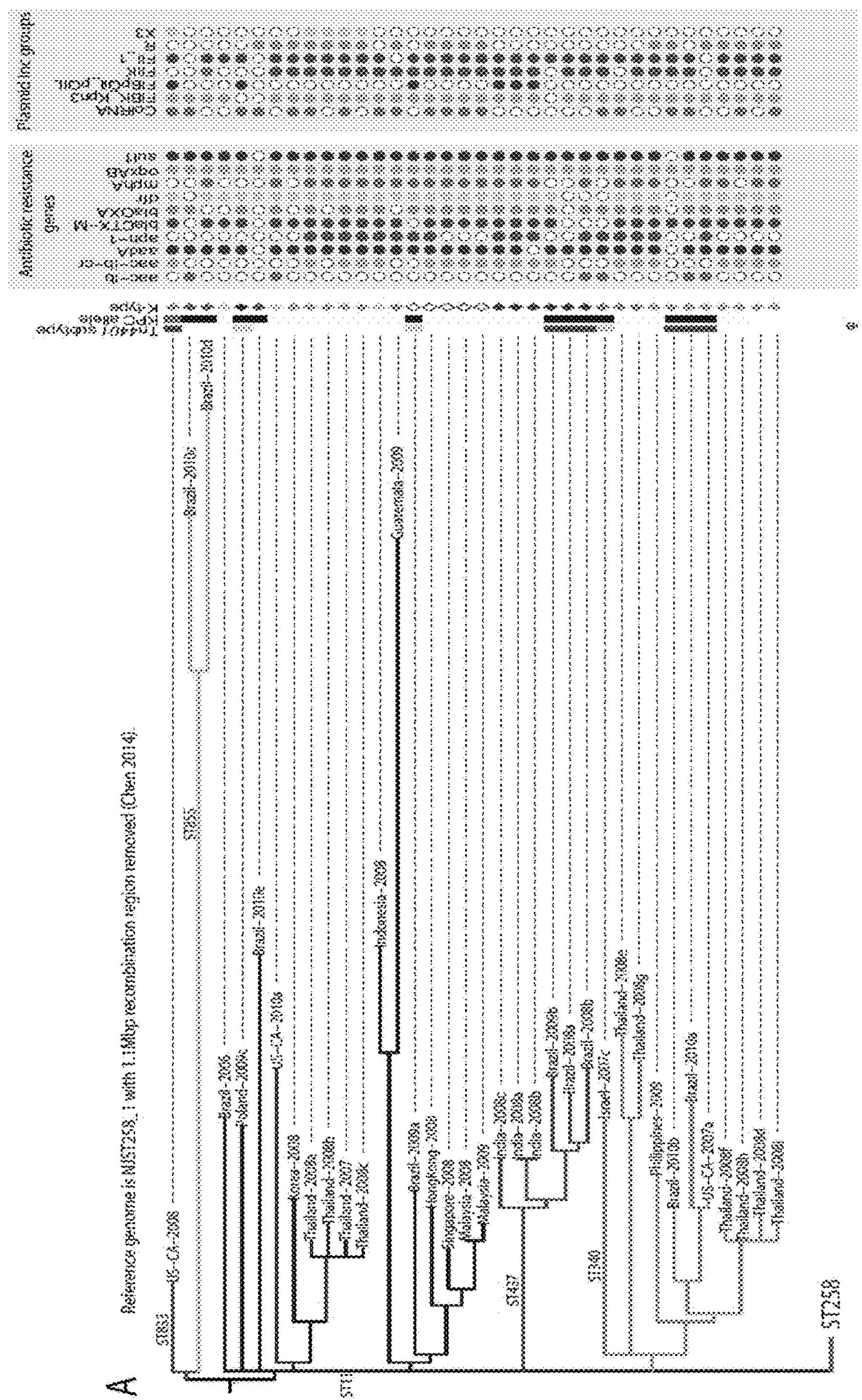
FIGS. 2A and 2B. Phylogenies of CG258 and ST258 with large recombined regions removed.
Figure 2:
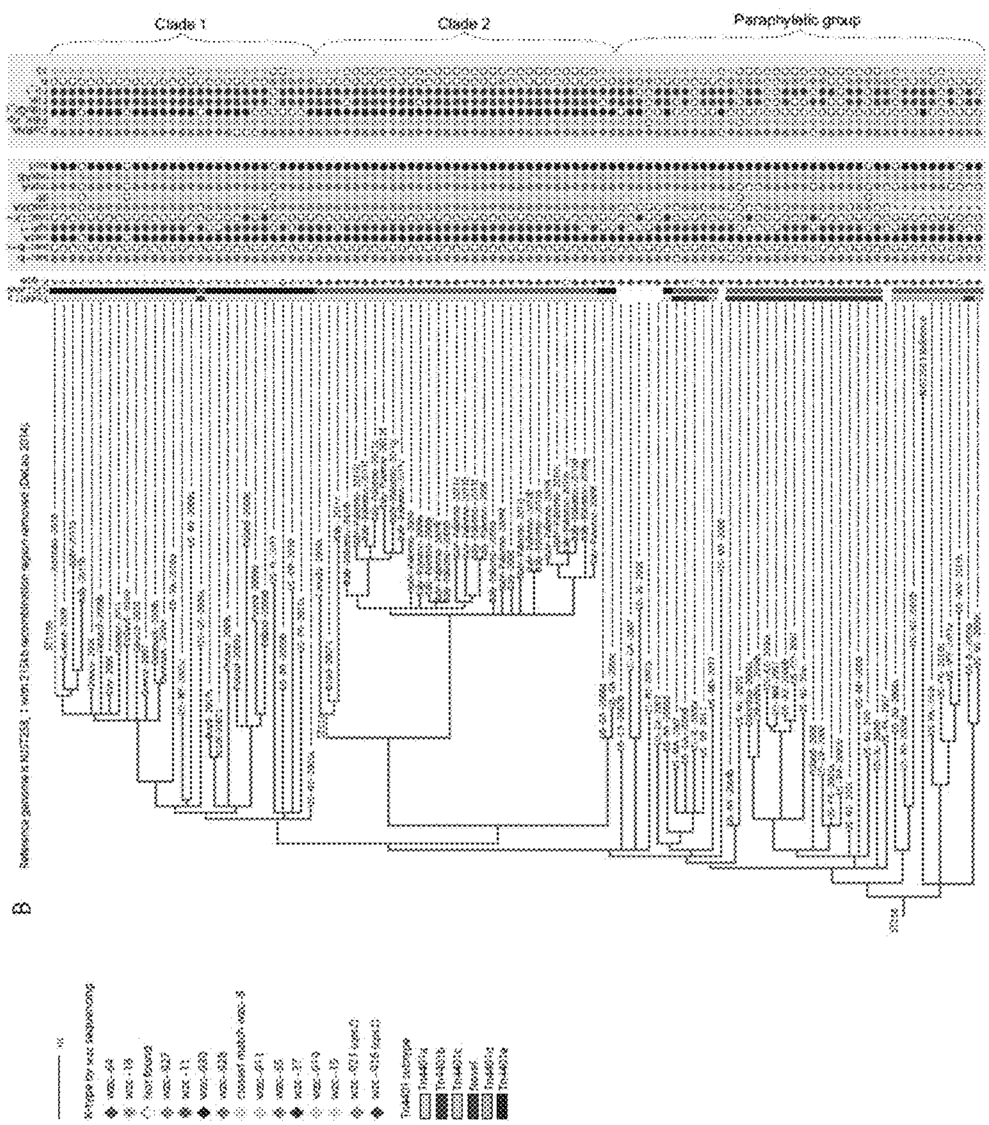
Figure 3:
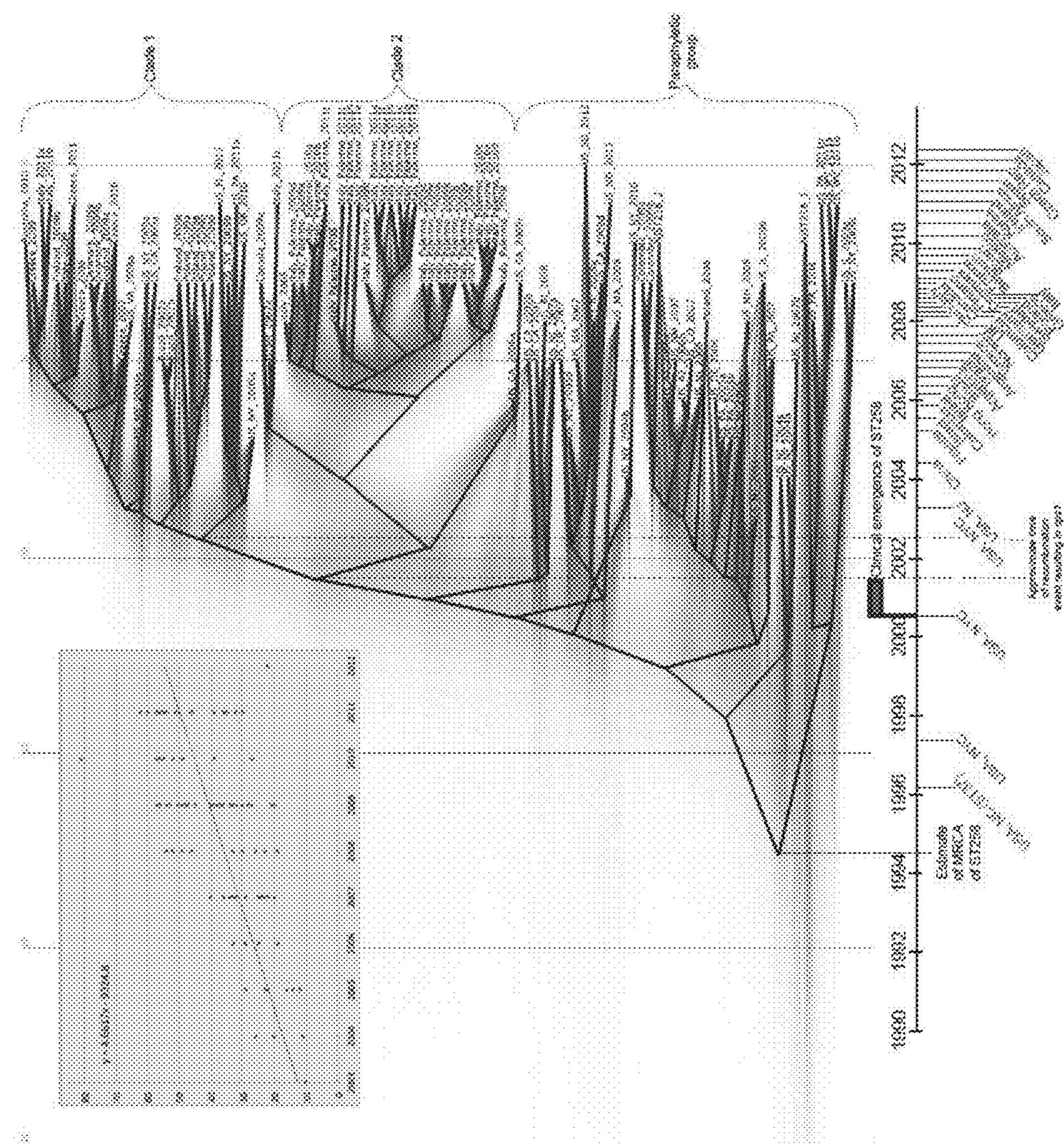
FIG. 3. Projecting the evolutionary history of ST258. BEAST analysis based on 1,425 core genome SNPs in 101 ST258 isolates with NJST258_1 reference genome, with the 215 kb region of recombination [15] masked, gives temporal context to the emergence of ST258, with key events and initial reports of KPC-producing *K. pneumoniae* in different countries plotted. Blue font indicates reports of KPC-producing *K. pneumoniae*, brown font is ST258. Green shading on the phylogeny shows lines of iterations of Bayesian analyses. The mean mutation rate of *K. pneumoniae* ST258 is $1.03\times10^{-6}$ (95% HPD $8.09\times10^{-7}$ to $1.24\times10^{-6}$). The TMRCA for the ST258 clade is approximately 20 years ago, around 1995. The plot inset is a root-to-tip analysis of SNP accumulations for each isolate since the MRCA of ST258. The slope of the fit line is 4.66, which is close to the mutation rate calculated by BEAST (($1.03\times10^{-6}$ substitutions per site per year)×(3.8 Mbp core genome size)=3.9 SNPs per year).

When reads from the 101 isolates in the ST258 group were mapped to the complete NJST258_1 (Table 1) chromosome, the ~215 kb region of homologous recombination [15] was identified by its high SNP density; 971 out of the total 2,396 SNPs fell in this region. This region was masked from the NJST258_1 reference to generate a refined ST258 SNP matrix. Compared to the entire collection, the core genome of ST258 is considerably larger at 3.8 Mbp (Table 1) due to more genome content in common, emphasizing the clonality of this group. The refined SNP matrix was used in both maximum parsimony and Bayesian (BEAST) analyses (FIGS. 2B and 3). Resulting phylogenies showed comparable overall topologies with the monophyletic Clades 1 and 2 originally defined by DeLeo et al. [15] conserved, and also sharing a common ancestor of their own. The remaining Emergence and Evolution of ST258 with KPC Bayesian analysis estimates the time to most recent common ancestor (TMRCA) of the global ST258 group as 17.2 years before the most recent isolate collected in 2012, or around 1995 (95% highest posterior density [HPD] 12.3 to 23.1 years, FIG. 3), slightly different from the conclusions of Gaiarsa et al. [17], who calculated the year 1997. From this study, US-NJ-2003 is the earliest confirmed ST258 to date. Previous reports have linked ST258 to a KPC-producing hospital outbreak in New York City in April, 2000 [21], suggesting that ST258 emerged as clinically significant just 5 years after origination. Notably, the first KPC-producing isolate identified was a ST37 strain collected in 1996 in North Carolina [4], contemporaneous and proximal with estimates of the first ST258 strains. The estimated time of the recombination event resulting in one of the alternate cps loci [15] is around 2001 to 2003. The inventors observed a strong correlation in the KPC-producing ST258 between cps1-containing isolates with KPC-2 (95%), and cps2-containing isolates (all in Clade 1) with KPC-3 (97%, FIG. 2), suggesting the KPC gene point mutation occurred in the common ancestor to Clade 1 between 2001 and 2003 as well. KPC-3-producing *K. pneumoniae* were first collected around this time [22], likely from ST258 strains [21], supporting this idea.

To enhance the collection of ST258 genomes, published sequence reads from 83 ST258 isolates mostly collected from the northeastern U.S. (NCBI SRA database study SRP036874, [15]) were added to the analysis with the masked NJST258_1 reference genome. A total of 2,282 SNPs were identified among all 186 ST258 isolates and were used in a maximum parsimony analysis and a second BEAST analysis that estimates TMRCA at 16.4 years before the 2012 isolate (95% HPD 12.8 to 20.6 years), both of which corroborate previous estimates. The inventors also incorporated the sequence data of 22 isolates from the NIH outbreak in 2011 [23] to illustrate the phylogeny of all 208 isolates. The publicly available genomes fall interspersed with ours throughout the phylogeny, showing that isolates from the northeastern U.S. and Canada genetically reflect a global isolate collection, supporting a northeast U.S. origination or highlighting the region as a hub of global travel. Clade 1 includes 29 publicly available genomes and remains monophyletic with four SNPs common to all. Clade 2 no longer has SNPs in common with the Georgia isolates on a basal branch in FIG. 2 (Clade 2 bottom branch), and these isolates were the only KPC-2 producers that fell in Clade 2. The NIH outbreak isolates clustered in their own tight clade, but monophyletic, having five SNPs in common, with the clade of Palermo, Italy, outbreak isolates.

The inventors' SNP phylogenies corroborate transmission of strains previously suggested to have epidemiologic linkages and highlight previously unrecognized transmission events. In addition, by juxtaposing variable genetic features alongside the SNP-based phylogeny, the inventors obtained further insight into epidemiologic and genetic transmission events. For example, 13 isolates, most collected from patients with a recent history of travel or healthcare exposure in Greece, clustered together despite being collected from diverse locations including Australia, Denmark, Finland, Greece, and Italy (FIG. 2, Clade 1) [24-26]. The small distance (average pairwise distance 21 SNPs) found among these isolates and shared genetic features indicate a common source. Also, an isolate collected in 2008 from Florence, Italy, unexpectedly clusters tightly with 27 isolates from a multi-institutional ST258 outbreak in Palermo, Italy. This isolate, Italy-2008, was the first ST258 identified in Italy, and was previously linked to Israel [27].

Mobile Elements

The KPC gene, $bla_{KPC}$, is carried on a highly mobile transposable element, Tn4401 [28] that is passed both vertically through bacterial clonal expansion and horizontally between unrelated strains. Tn4401 subtypes have different deletions upstream of $bla_{KPC}$ that confer different promoter regions to the gene [29]. Tn4401b is the full-length Tn4401 element; different deletion events result in conversion to a, c, d, and e subtypes. Sequential deletions could be responsible for subtype conversions; the most plausible based on deletion size are conversions from a or d to c or e, and c to e. However, selection may be against conversions from Tn4401a or d as strongest $bla_{KPC}$ expression occurs with the promoters present in these subtypes [29]. Vertical transfer of $bla_{KPC}$ within a limited period of time and on a local or regional level has been observed previously [30, 31]. Parsimony analysis of the data suggests that the vertical transfer of Tn4401 in ST258 has played a significant role in $bla_{KPC}$ dissemination (FIG. 2B). The paraphyly that characterizes isolates outside of Clades 1 and 2 suggests that the ST258 MRCA carried the full length Tn4401 b with $bla_{KPC-3}$ and that deletion events in Tn4401 and point mutations in $bla_{KPC}$ occurred before various clades diverged. Occasionally, independent acquisition by horizontal transfer is evident where an isolate carries Tn4401 b while the majority in its clade have another subtype, as is the case for US-GA-2009a (FIG. 2B, Clade 1), which also differs in $bla_{KPC}$ type from its closest relatives, and possibly for US-IL-2009a (FIG. 2B bottom, cluster containing Tn4401d). US-NY-2005a carries both a Tn4401a and Tn4401b. This isolate may still be carrying the ancestral b and acquired a, or may have acquired b in addition to its a, or this may be the result of a transposon duplication event. Independent Tn4401 acquisition in ST258 is indicative of persistent selective pressure for this dominant strain to harbor $bla_{KPC}$ or genes that may be acquired along with it (i.e. other antibiotic resistance genes carried on the same mobile element).

Conservation of plasmid incompatibility groups within ST258 may reflect the successful vertical transmission of particular plasmids. The predominant incompatibility groups in ST258 are $FIB_K$ (pKPN3, in 96% of isolates), ColRNA (in 95%), FII (in 86%), and $FII_K$ (in 82%). The KPC-encoding plasmid pKpQIL described in ST258 outbreaks in Israel and Italy [32, 33] and pKpQIL-like plasmids in New Jersey and New York isolates [34] are multi-replicon plasmids of both incompatibility groups $FII_K$ and FIB (pKpQIL). Within Clades 1 and 2, nine isolates do not have these plasmid types, one of which is US-GA-2009a that appears to have lost and reacquired Tn4401 (FIG. 2B). The inventors' phylogeny suggests that the MRCA to Clades 1 and 2 harbored a pKpQIL-like plasmid that was then lost as few as five times. The FIB type of pKpQIL plasmids is absent from most isolates outside of these clades. The plasmid type profiles of Clades 1 and 2 are very similar overall; most isolates have five of the seven types illustrated in FIG. 2B. IncX appears to have been lost in the Italy-Palermo isolates (and also appears to have been lost in another clade in the paraphyletic group). Incompatibility types are diverse in the paraphyletic group of isolates. Plasmids, therefore, likely add considerably to the *K. pneumoniae* species pan-genome. The seven $bla_{KPC}$-negative ST258 isolates may have lost a KPC-encoding plasmid, as has occurred before [35], however, no clear incompatibility group pattern correlates strongly with its loss. Three of them appear to carry a pKpQIL-like plasmid. Likewise, outside of ST258 in CG258, three Tn4401-negative isolates in ST437 also appear to carry a pKpQIL-like plasmid. And again, no clear incompatibility group pattern correlates strongly with Tn4401 carriage. These observations are not surprising as Tn4401 is associated with many different plasmid types owing to its high mobility [36-39].

An abundance of resistance genes are harbored by CG258, presumably on various plasmids (FIG. 2). These genes encode mechanisms of resistance to quinolones (aac-lb-cr or oqxAB identified in 100% of isolates), aminoglycosides (aac-lb, aadA, or aph-1, in 99% of isolates), β-lactams (by β-lactamases encoded by $bla_{KPC}$, $bla_{CTX-M}$ or $bla_{OXA}$, in 96%), trimethoprim and sulfonamides (dfr or sul1 in 93% and 94%), and macrolides (mphA, in 81%), many of which were also identified, although less frequently, in unrelated *K. pneumoniae*. The antibiotic resistance profile these genes confer is highly similar in ST258 and the rest of CG258. At the gene level, ST258 differs from the rest of CG258 in $bia_{KPC}$ and $bia_{CTX-M}$ status, and in aac-lb and aac-lb-cr status. The high frequency of $bia_{CTX-M}$ in CG258-non-ST258 may be due to sampling bias, however these sequence types are known to often carry β-lactamase genes [9-11]. Interestingly, the quinolone resistance gene aac-lb-cr, in many of the CG258-non-ST258 isolates but in only two ST258 isolates, is two nucleotides different from the aminoglycoside resistance gene aac-lb, present in almost all ST258 and in only six of the rest of CG258 isolates. Both of the aac-lb-cr-positive ST258s are aac-lb-negative, and vice versa for the aac-lb-positive CG258-non-ST258s, suggesting that these two genes are not independently acquired in the two groups, but the MRCA to all carried one and point mutations result in the other. If this is the case, the point mutations have happened in more than one lineage in both groups.

The frequent point mutations observed in CG258 in aac-lb and aac-lb-cr are interesting in that all CG258 isolates have the fluoroquinolone resistance-conferring mutations in GyrA (Ser83 to Ile) and ParC (Ser80 to Ile), the DNA gyrase and topoisomerase enzymes on which fluoroquinolones act, and almost all have another aminoglycoside resistance gene, aadA or aph-1. This resistance is important considering fluoroquinolones and aminoglycosides are drugs of choice for urinary tract infections (UTIs), the major pathology caused by ST258. Also, all CG258 isolates carry the genes for the OqxAB efflux pumps, generally conferring low-level resistance to fluoroquinolones. The apparent selection pressure for multiple mechanisms of similar resistance may be due to the slightly different phenotypes conferred by each.

The inventors screened the isolate genome assemblies for several virulence genes recently described in the highly virulent capsule type K2 Kp52.145 isolate [40] to determine their potential contribution to pathogenic success. Within CG258, the inventors found several instances of colibactin genes, which encode a genotoxin that induces host DNA damage, and conjugation machinery of type IV secretion systems (T4SS), which is not surprising given CG258's plethora of plasmids. Of note, the inventors found two isolates that carry genes similar to the newly described pld1 gene encoding a phospholipase D protein involved in lipid metabolism [40]. PLD1 was found to be prevalent in highly virulent *K. pneumoniae* isolates or those known to cause severe infections [40]. In the inventors' collection, ST39 (US-TX-2011) and ST719 (US-VA-2008b), but no CG258, carried genes similar to pld1.

Factors Impacting Extracellular Interaction

Among the four SNPs that separate all ST258 from the rest of CG258, one is non-synonymous in a gene encoding a transcriptional regulator protein in the multiple antibiotic resistance repressor (MarR) family. Members of this family such as SlyA in *Salmonella* and MarR in *E. coli* and *K. pneumoniae* (different from this MarR family protein) have a helix-turn-helix motif and form homodimers that bind DNA at marboxes to block expression of genes. MarR family proteins also bind stimulatory ligands thought to result in a conformational change averting its bond with DNA. In this way, MarR family proteins mediate metabolic responses to a cell's environment. Mar regulons have many regulatory functions in many taxa, including multidrug efflux pump and outer membrane porin production, stress tolerance, toxin degradation, and many other virulence factors [41]. MarR is a repressor of the pleiotropic marRAB regulon. MarA is a gene expression activator that in *E. coli* is involved in regulation of over 60 genes [42, 43], and binds intrinsic copper released upon disruption of cellular membrane processes [44]. MarA is closely associated with and interacts with several other pleiotropic transcription regulators, including SoxS, Rob, and RamA, which all contribute to regulation of the AcrAB-TolC efflux pump genes implicated in fluoroquinolone and tigecycline resistance [42, 45-47]. Overexpression of RamA results in lipopolysaccharide modifications that alter the outer layer of the cell, decreasing its susceptibility to host-derived antimicrobial peptides as well as polymyxins, and increasing its evasion of phagocytosis by host macrophages [46]. The SNP in the marR-family gene in ST258 isolates, which appears to be 100% specific and 100% sensitive to ST258 by in silico validation, confers Ser34 to Phe amino acid change in the homodimerization region of the protein. This substitution may affect the proteins' ability to form the homodimer, which in turn would affect its ability to bind ligands or marboxes. It is conceivable that, considering the potential interconnection of this regulator with others, this amino acid substitution may result in significant metabolic changes in ST258. Indeed, this MarR family protein is very highly conserved among *K. pneumoniae*, signifying its functional importance. The only other amino acid changes found in the species are in KP5-1 and 342, both plant-associated isolates, and interestingly, in all of CG258. The Arg4 to Ser mutation in CG258 occurs in a seemingly insignificant domain of the MarR family protein; however this change may affect protein folding and therefore function. Additionally, isolates in CG258 share a synonymous nucleotide substitution in the gene (another rare occurrence), C408 to T, which appears to be 100% specific and 100% sensitive to CG258 by in silico validation. Although it appears that CG258 inherited this gene from a relative of ST1628 in the 1.3 Mbp recombination event [17], the ST1628 isolate does not share this marR-family gene SNP or the Arg4 to Ser amino acid change with CG258.

The inventors capitalized on the specificity of these SNPs in the marR-family gene by developing assays to target them (Table 2). These assays could be used in real-time PCR or in amplicon sequencing to detect a CG258 and/or ST258 strain. The inventors screened them as dual-probe real-time PCR assays across a subset of the collection, and found them to be 100% specific and 100% sensitive, correctly typing 48 CG258 and 24 ST258. The ST258 assay was also robust to *K. pneumoniae*, correctly typing 49 non-ST258 isolates comprising more than 20 different sequence types. The CG258 assay detected 13/15 non-CG258 isolates. The two it missed are the divergent US-PA-2001 and US-GA-2009b; these two isolates contain SNPs in the marR-family gene in the assay region.

Some embodiments of this technology further comprise the amplification of at least a portion of the marR gene. For example, the method may comprise obtaining a sample and amplifying and/or detecting the presence of the a member of the marR gene family or a member of the MarR protein family in the sample. In some aspects, the method may include amplifying the marR gene family member from nucleic acids extracted from the sample using one or more of the oligonucleotides recited below (e.g., SEQ ID NOs: 1-4 and/or 5-8).

TABLE 2

SNP mutations and real-time PCR assays to detect CG258 and ST258. Lowercase letters in the probes indicate the targeted SNP state.

| Gene | SNP | SNP Specificity | Assay | Primer/Probe Sequence | Assay Sensitivity/ Specificity |
|---|---|---|---|---|---|
| marR-family | C101 to T | ST258 | ST258_F | ATGGTGGTGCGCCAGTG (SEQ ID NO: 1) | To ST258: 100%/100% To non-ST258: 100%/100% |
| | | | ST258_R | GCTGACCGAGACGTTGTC (SEQ ID NO: 2) | |

TABLE 2-continued

SNP mutations and real-time PCR assays to detect CG258 and ST258. Lowercase letters in the probes indicate the targeted SNP state.

| Gene | SNP | SNP Specificity | Assay | Primer/Probe Sequence | Assay Sensitivity/ Specificity |
|---|---|---|---|---|---|
| | | | ST258-T_FAMBHQ+ | CATTATTGACTtCG CTATCA (SEQ ID NO: 3) | |
| | | | nonST258-C-TETBHQ+ | CCATTATTGACTcC GCTAT (SEQ ID NO: 4) | |
| marR-family | C408 to T | CG258 | CG258_F | ACGGCAGGCGATTT GATTTAACG (SEQ ID NO: 5) | To CG258: 100%/100% To non-CG258: 87%/100% |
| | | | CG258_R | AGCTGCGTGATCGA GACCTATC (SEQ ID NO: 6) | |
| | | | CG258-A_FAMBHQ+ | CGCTGAAGGTaGCG AGAT (SEQ ID NO: 7) | |
| | | | nonCG258-G_TETBHQ+ | CTGAAGGTgGCGAG ATC (SEQ ID NO: 8) | |

A second transcription regulator that potentially shapes the CG258 phenotype is the repressor OqxR of the OqxAB efflux pump genes. The oqxAB locus, originally described on a plasmid in *E. coli* [48], is widely reported in *K. pneumoniae* [49]. Bialek et al. recently described a mutation in OqxR that results in overexpression of OqxAB, which contributed to antibiotic resistance in *K. pneumoniae* clinical isolates, and showed that various classes of antibiotics (fluoroquinolones, chloramphenicol, and 1-lactams) are among the OqxAB pump substrates [50]. Zhong et al. also associate OqxAB with tigecycline resistance [47]. The inventors found a mutation in OqxR in CG258, Val130 to Ala, due to SNP T389 to C that appears to be specific to CG258. (ST11 HS11286, Genbank accession CP003200, does not have the oqxAB locus, however, so it does not appear to be 100% sensitive to CG258.) Veleba et al. found Val130 to Ala, but did not associate this mutation with increased or decreased repression citing confounding effects of other metabolic regulators; however, they mention this mutation is part of current experiments [51]. Italy-Palermo-2009g (ST258) also has a deletion of 13 bases that results in a premature stop codon, likely resulting in a defective repressor protein. Three other isolates outside CG258 also have deletions resulting in truncated proteins (two ST14 isolates and US-GA-2009b of novel sequence type), indicating that mutation of this repressor may be a common mechanism of increased antibiotic resistance in clinical isolates.

The inventors characterized the cps locus and outer membrane protein (OMP) profiles of the collection, two complex systems that encode multiple proteins in direct contact with the extracellular environment and potential antigenic targets for the host immune system. *K. pneumoniae* capsules play an important role in virulence, and CPS modification has been described in other species to allow evasion of host immune detection [52, 53]. The inventors found a remarkable degree of cps diversity in the collection, with over 35 different variants falling into over 25 different K-types (FIG. 1). CG258 alone contains 18 different variants, of which only seven have been characterized [15, 18], and several have no exact match in the wzc and wzi gene sequence databases. Recombination in the cps region is apparent throughout the phylogeny where K-types (by wzc and wzi sequence) match between distantly related isolates (FIG. 1). In one case, three distantly related isolates, Brazil-2010e (ST11), US-WA-2010 (ST147), and US-TX-2001 (novel ST), have the same full length cps sequence highly similar to Genbank accession number KR007672 from another ST11 isolate [18]. Interestingly, characterization of the full cps loci showed that all three of the ST37 isolates are characterized by different cps loci, and each is shared with CG258 strains; two are shared among isolates in this study (FIG. 1), and one cps locus was characterized in a ST11 isolate previously [18]. In more than one case, the inventors observed K-type matches by wzc or wzi sequence, but sequence divergence in other regions of the cps locus. Two distantly related isolates share a wzc sequence but not wzi (FIG. 1), and in two cases wzc and wzi sequences matched between isolates but the full locus did not match.

Figure 4:
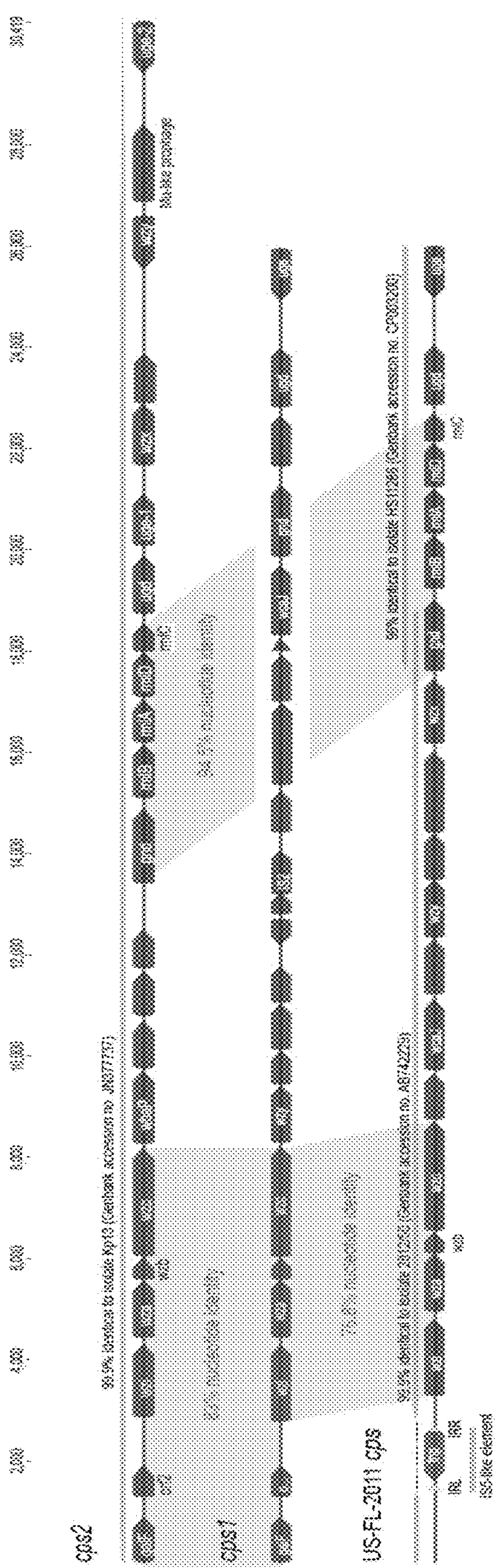
FIG. 4. Characterization of three cps loci found in ST258 isolates. Regions of identity are shaded and GenBank BLAST matches labeled. Putative glycosyltransferases are in green and hypothetical proteins are in blue. The IS5-like element disrupting the 5' region of the US-FL-2011 cps locus is in red and yellow.

The majority of the ST258 isolates maintained either cps1 or cps2. The inventors' genomic data second the suggestion by DeLeo and colleagues [15] that a ST258 lineage recombined with DNA from a ST42 strain and acquired the cps1 locus primarily found in ST258 Clade 1. The ST42 isolate in the collection was collected from a Brooklyn hospital in 2004, and the ST42 isolates described in the DeLeo study were collected from New York City hospitals in 2001 to 2002. The inventors' Bayesian analysis calls the cps1 clade monophyletic; the recombination event that introduced cps1 in ST258 likely occurred once in a common ancestor to the clade around 2002 (FIG. 3), possibly in the New York City area. However, the inventors' observation of the strong correlation between cps1-containing ST258 with KPC-2, and cps2-containing ST258 with KPC-3 (FIG. 2), taken in the context of the entire ST258 phylogeny, leads us to hypothesize the $bla_{KPC}$ point mutation occurred around the time of the cps recombination, rather than from independent acquisition of Tn4401, as DeLeo and colleagues suggest [15]. Within Clade 1, the analysis also identified a third ST258 cps locus in US-FL-2011. This locus is identical to part of the capsule type K23 isolate, 2812/50 (GenBank accession no. AB742229), but is disrupted by an IS5-like element in its 5' end, is missing galF and orf2, and in part resembles HS11286 (FIG. 4). US-FL-2011 was collected as part of a hospital outbreak investigation, suggesting these additional cps modifications do not impact ST258 success.

*K. pneumoniae* outer membrane proteins not only provide structure to the membrane and allow transport of iron, nutrients, and antimicrobial agents via their pores, but also contain extracellular loops that affect surface adhesion and invasion, biofilm formation, and host immune detection [54-56]. The inventors examined sequence of the major porin proteins KpOmpA, OmpK26, OmpK35, OmpK36, and OmpK37 to explore differences in the collection (FIG. 1). KpOmpA demonstrated little variation regardless of sequence type; 95% matched GenBank accession WP_002898408. Only five other variants comprised the rest. KpOmpA interacts with plasmid conjugation machinery; its presence increases frequency of conjugation [56]. KpOmpA can also form two different conformations, resulting in two different membrane pore sizes, offering a form of variation in the protein [56]. OmpK26 was also conserved among isolates; 86% matched GenBank accession WP_002916050, and only five other variants comprised the rest. OmpK26 is indispensable to a cell when OmpK35 and OmpK36 proteins are deficient [57].

Figure 5:
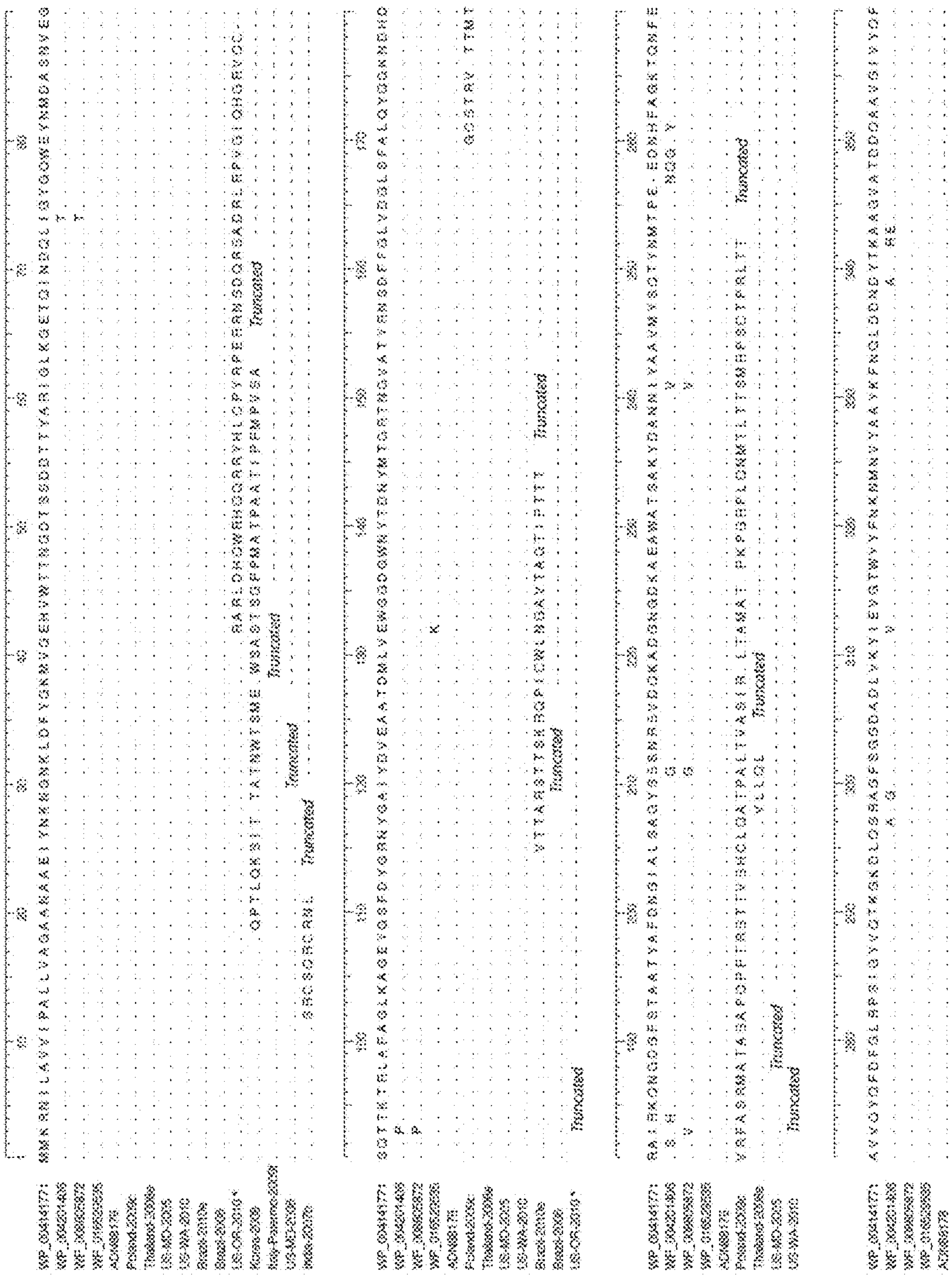
FIG. 5. OmpK35 alignment of all alleles found in the 167 isolates. Sequences are labeled by Genbank accession number when they're an exact match. WP_004141771 was the most frequently found complete protein in the isolates, and was used as the reference in the alignment. Dots are conserved sites, dashes are sites downstream of a premature stop codon. *US-OR-2010 represents all ST258 isolates in the study. These variants are in the divergent isolates US-PA-2001 and US-GA-2009b, not shown in FIG. 1**.
Figure 6:
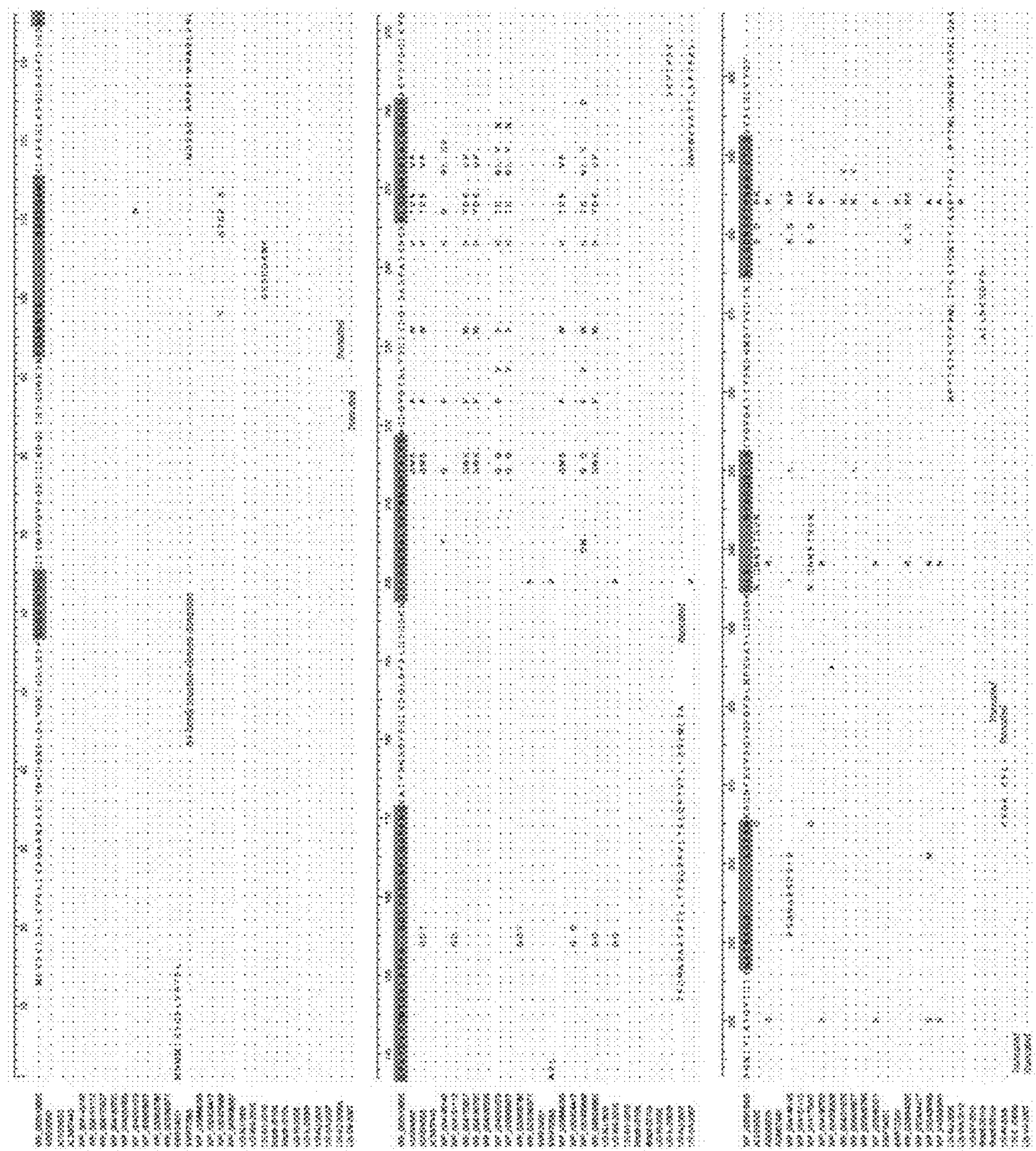
FIG. 6. OmpK36 alignment of all alleles found in the 167 isolates. 100% identity BLAST matches were not found for several sequences; sample names are used for these sequences. WP_002913005 was the most frequently found protein so was used as the reference. Sequence in green represents the extracellular loop regions of the protein. Dots are conserved sites, dashes are gaps or represent sites downstream of a premature stop codon. *This variant is not shown in FIG. 1; it occurs in ST258 isolate US-GA-2007. These variants are in the divergent isolates US-PA-2001 and US-GA-2009b, not shown in FIG. 1**.
Figure 7:
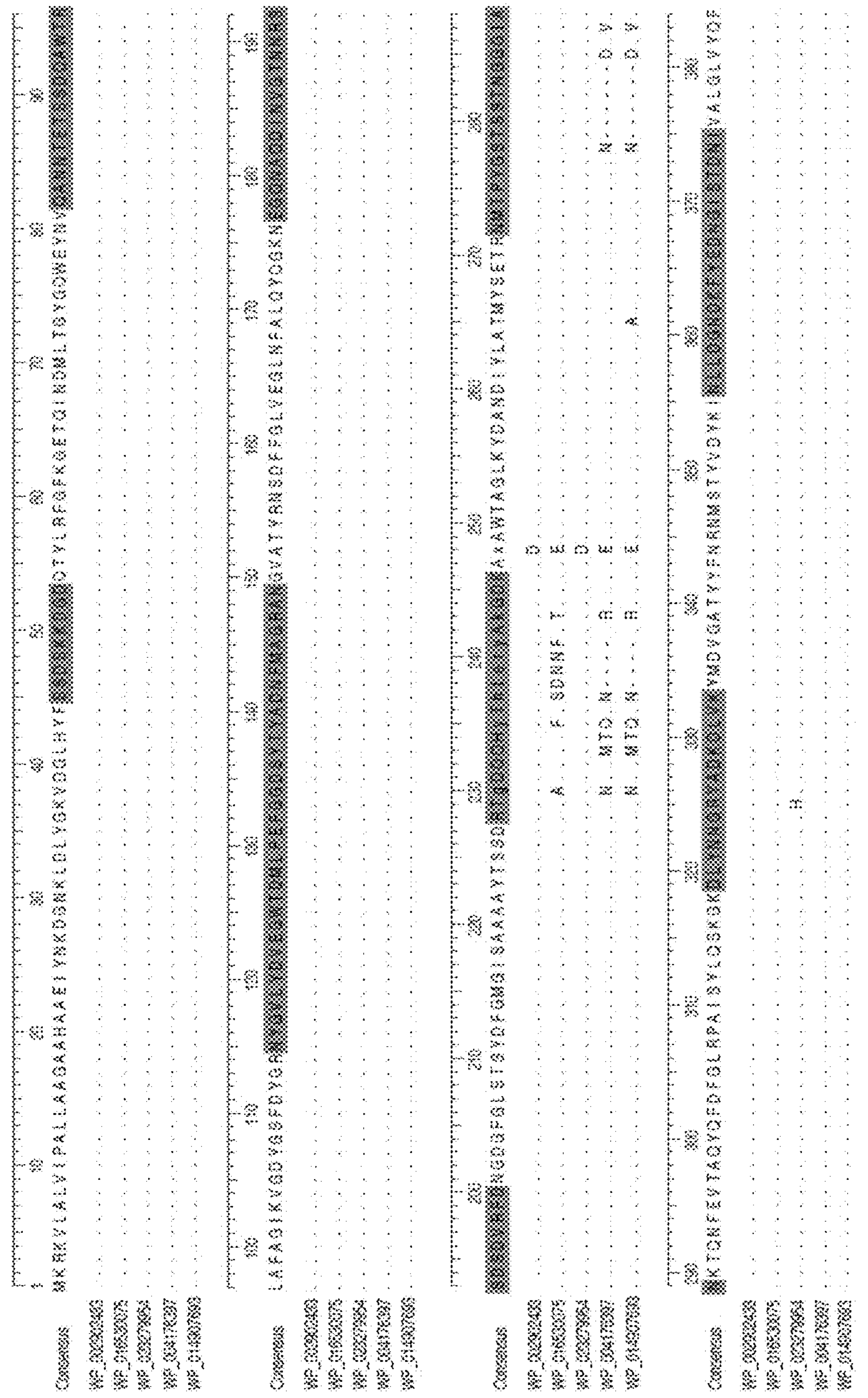
FIG. 7. OmpK37 alignment of all alleles found in the 167 isolates. Sequence in green represents the extracellular loop regions of the protein assumed from the structure of OmpF by Doménech-Sánchez et al. [59]. Dots are conserved sites, dashes are gaps. These variants are in the divergent isolates US-PA-2001 and US-GA-2009b, not shown in FIG. 1**.

All ST258 isolates in the collection shared an OmpK35 sequence containing a frame-shift that results in a premature stop codon and truncated protein. Although this mutation has been reported previously [58], the inventors found it exclusive to the ST258 group (FIG. 1). The resulting outer membrane porin loss increases β-lactam resistance [59] and in combination with a β-lactamase results in high levels of β-lactam resistance [60]. Several other isolates harbored truncated OmpK35 proteins (FIGS. 1 and 5), likely owing to OmpK35's allowance of carbapenem antibiotics across the cell membrane, and all harbored a β-lactamase gene, $bla_{KPC}$ (n=5 outside ST258), $bla_{CTX-M}$ (n=4), or $bla_{VIM}$ (n=1). OmpK36 displayed the most diversity (FIG. 1); 40 different variants were found, with amino acid variations concentrated in the extracellular loop regions of the protein (FIG. 6), presumably diversifying *K. pneumoniae*'s interactions with the environment and potentially influencing host immune response and adherence of the cells to host surfaces [55]. Most CG258 shared a similar OmpK36 matching GenBank accession WP_002913005 (76% of ST258 and 76% of CG258), with the remainder sharing 12 variants (FIG. 6). In the 155 isolates for which a complete OmpK36 protein was characterized, the average pairwise distance is 3 amino acids. Each unique variant differs by an average of 13 amino acids. Seven isolates have a premature stop codon and putatively non-functioning protein, five of which are ST258. In one isolate, an IS4-family insertion disrupts the 5' end of the gene. These five mutations do not appear to have clonally spread, as each is unique and these isolates do not fall in the same clades. This may reflect selection against OmpK36 truncation; indeed previous reports associate OmpK36 loss with increased susceptibility to phagocytosis [55]. The OmpK37 sequences of 100% of CG258 isolates match Genbank accession WP_002902433, whose amino acid sequence shows extensions in extracellular loop regions (FIG. 7). Outside CG258, 26% of isolates carried this protein, and 66% match Genbank accession WP_004176397 or WP_014907693, which have shorter extracellular loops in regions L5 and L6. The two divergent isolates not shown in FIG. 1 both had unique protein sequences for all five proteins. The combination of the extended loop regions in OmpK37 and the absence of a functional OmpK35 are not unique to the ST258 group in this study, however only nine isolates outside ST258 have this profile. The combination of this profile with other characteristic features in ST258 likely impacts extracellular interaction with the environment.

Perfect examples of large homologous recombination events between unrelated strains resulting in new, more successful pathogens [61] are the evolutionary events that generated CG258 [17] and the ST258 strains [20], both results of single events that encompassed approximately 20% of the *K. pneumoniae* genome. Whether these events are the secrets to CG258 and ST258's success is unclear. Over the past decade, CG258 strains carrying carbapenemase genes, especially KPC-producing *K. pneumoniae* ST258, have become some of the most successful multidrug-resistant bacterial pathogens in healthcare settings throughout the world. Reports describe ST258's ability to overtake a previously established carbapenemase-producing *K. pneumoniae* strain within an institution in Greece [62], and to rapidly disseminate throughout a country and surpass a pre-existing KPC-producing *K. pneumoniae* population in Israel [13, 21]. As other KPC-producing *K. pneumoniae* preceded ST258, this suggests that KPC alone is not the driver of ST258's success, and that ST258 has other evolutionary advantages.

The combination of the aforementioned parsimony analysis and the coincident emergence of ST258 and KPC around 1995-1996 leads us to propose that ST258's common ancestor acquired KPC-encoding Tn4401 prior to dissemination. KPC-producing ST258 probably originated in the northeastern U.S., clinically emerging in hospital outbreaks as early as 2000. The subsequent success of ST258 has played a large role in the global dissemination of KPC through vertical transmission. The inventors noted two instances where it appears ST258 replaced its Tn4401 element through horizontal transmission. Why ST258 is closely linked to Tn4401 is unknown. Given that ST258 is a healthcare-associated pathogen, a likely contributor to its selection is the heavy use of carbapenem antibiotics. In the late 1980s and early 1990s, clinicians relied on carbapenems as a last resort to battle the increasing number of Enterobacteriaceae producing extended-spectrum beta-lactamases (ESBLs). While carbapenem use continued during the time of ST258's origination, a recent study by the Veteran's Health Administration noted 102% increase in carbapenem use in their acute care facilities between 2005 and 2009 [63]. This increase was also noted in other U.S. hospitals, and mirrors the rapid expansion of ST258. The use of other antibiotics within the healthcare setting, particularly fluoroquinolones and aminoglycosides used to treat urinary tract infections (UTIs), could also act as a positive selective force, considering that ST258 causes UTIs and typically carries resistance mechanisms to several other classes of antibiotics.

The global spread pKpQIL-like plasmids, responsible for much of ST258's Tn4401 carriage [32-34] demonstrates the tenacity of particular plasmids. This plasmid analysis suggests the most recent common ancestor (MRCA) of ST258 Clades 1 and 2 carried a pKpQIL-like plasmid and it is highly persistent. It is impossible to determine whether pKpQIL-like plasmids date back further than the MRCA of Clades 1 and 2 from the data. It may have been in older ancestors and lost, or acquired multiple times. The vertical fidelity those plasmid types show in Clades 1 and 2 suggests it is not easily lost.

The antibiotic resistance gene patterns of CG258 do not illuminate a particular profile responsible for ST258 clonal success. CG258 isolates are similar, with the exception of the SNP variant genes' aac-lb and aac-lb-cr mutual exclusivity. CG258 non-ST258 isolates have aac-lb-cr, conferring fluoroquinolone resistance, while most ST258 have aac-lb, conferring aminoglycoside resistance. Both groups carry at least one other aminoglycoside resistance gene and have the fluoroquinolone resistance mutations in gyrA and parC. Both aminoglycosides and fluoroquinolones are a highly used drug for UTIs, a common pathology of CG258 strains, and these multiple mechanisms for resistance to the same classes of antibiotics may offer higher resistance levels or resistance to different drugs within the same classes. Additionally, the amino acid change in the OqxAB repressor protein OqxR found in this study specific to CG258 isolates (Val130 to Ala) could suppress its repressor functions, resulting in overexpression of the OqxAB efflux system and high-level fluoroquinolone resistance. A similar mutation, Val102 to Gly, was responsible for a multidrug resistance phenotype in *K. pneumoniae* clinical isolates [50]. The deletion mutations that result in truncated OqxR proteins in three other clinical isolates studied here suggest a non-functional OqxR is not lethal and may offer a fitness advantage in certain circumstances.

Two other potentially important mutations documented in this study, one in CG258 and the other specific to ST258, occur in a MarR family transcription repressor protein. MarR family proteins have been described in many species as responders to environmental stimuli such as host immune factors, toxins, antibiotics, and stress factors [41]. All CG258 isolates share a SNP in the marR-family gene resulting in amino acid change Arg4 to Ser. Although this change occurs outside of functionally characterized domains of the protein, it may affect protein structure and therefore function. The mutation specific to ST258 results from one of the four point mutations in the core genome separating ST258 from the rest of CG258. The resulting amino acid change, Ser34 to Phe, occurs in the homodimerization region of the protein. Given that this protein is highly conserved in the *K. pneumoniae* species, these amino acid changes may be significant. The Ser34 to Phe mutation may affect the ability to form a complete functional protein, bind stimuli ligands, or bind DNA to repress transcription. It is conceivable that suppression of the MarR family protein results in overexpression of systems that give ST258 a fitness advantage in particular environments. Further experiments to test this are underway. The SNP in ST258 that confers the amino acid change is now the target of a sensitive and specific assay to detect ST258. Additionally, another SNP in the marR-family gene encompassing all CG258 is the target of a second assay to detect CG258. SNPs are stable mutations, especially in highly conserved genes, and can be detected using a variety of molecular methods. Here the inventors have shown that real-time PCR can be used for rapid detection and typing of *K. pneumoniae*. Both assays show 100% sensitivity and specificity, so are ideal for easy, cost-effective surveillance for ST258 and CG258.

Capsule modification allows adaptation to changing environments [53], and the variety of cps genotypes in the collection indicates that the capsule locus is highly mobile. IS elements reside within the cps region of some strains, potentiating the formation of new capsule types [18]. CG258 has at least 23 different capsule types, 11 uncharacterized, and ST258 at least three; one of which, firstly described in this study, lacks two highly conserved cps genes apparently deleted by integration of an IS element. Despite this disparity, the success of the strain does not appear to be affected. Some isolates had inconsistent genotypes in the capsule genes wzc and wzi: two shared a wzc but had different wzi genotypes, and some had identical genotypes but clearly different capsule types. These data, considered with the discovery of IS elements in several cps loci [18], should factor into interpretations of capsule typing by wzc and wzi sequencing. Several different capsule types characterize successful *K. pneumoniae* clinical pathogens, and as more isolates are sequenced, more and more types will undoubtedly be found. The limited number of capsule types characterizing ST258 make the capsule a good target for a vaccine, however surveillance will be critical to detect any future recombination events.

The functional repertoire of outer membrane proteins in *K. pneumoniae* is vast and complex, but undoubtedly includes functions critical to environmental adaptation. Depending on the allele, OmpA may cause more or less invasive capacity, immune evasion, adherence to particular cells or surfaces, and can affect frequency of plasmid conjugal receipt from donors [56]. The conservation in OmpA sequence in the collection may reflect selection against mutation. Likewise, OmpK26 was conserved despite the isolate diversity, suggesting selection against mutation. OmpK26 compensates for dual OmpK35 and OmpK36 loss in clinical isolates [57], and may play a role in compensating for OmpK35 loss alone, which the inventors found is common in this collection of isolates. Conversely, the inventors found 40 different OmpK36 sequences in the isolates, with amino acid variation concentrated in the extracellular loop regions. Selection for variation in OmpK36 may slow host recognition, or allow colonization of new tissues, as these are functions in the OmpK36 repertoire [55]. Outer membrane protein analysis revealed a profile in all ST258 that includes a truncated OmpK35, which would be expected to have deleterious effects on fitness, but may provide a degree of positive selection in a host environment where OmpK35 is not typically expressed [64]. In these analyses, protein truncation was much more frequent in OmpK35 than in other outer membrane proteins. The OmpK37 sequence found in the ST258 and CG258 isolates contains insertions in the extracellular loop regions, which again may impact interaction with its environment. ST258's OMP profile, including OmpK35 loss and OmpK37 extended loops, could contribute to its enhanced ability to persist in a host or healthcare environment.

The inventors' data underscore the usefulness of whole genome sequencing in epidemiology, evolutionary history, and specific genetic attributes of pathogens. The genomic analyses of KPC-producing *K. pneumoniae* that is presented in this study provide further insight into the evolution and rapid spread of the globally dominant strain, ST258. The inventors show that in addition to the large recombination events that gave rise to CG258 and ST258 [17, 20], key point mutations may also play a significant role in the evolution of these strains. Based on these SNPs, the limited number of cps variations and the OMP profile that is conserved within ST258, this work also provides information important to surveillance and to development of a vaccine to specifically target ST258 and contain the KPC-producing *K. pneumoniae* pandemic.

The following references are hereby incorporated by reference in their entirety for any purposes.

1. Centers for Disease Control and Prevention. Antibiotic Resistance Threats in the United States, 2013. Centers for Disease Control and Prevention, 2013.
2. Jacob J T, Klein E, Laxminarayan R, Beldavs Z, Lynfield R, Kallen A J, et al. Vital Signs: Carbapenem-Resistant Enterobacteriaceae. MMWR Morb Mortal Wkly Rep. 2013; 62.
3. Patel G, Huprikar S, Factor S H, Jenkins S G, Calfee D P. Outcomes of carbapenem-resistant *Klebsiella pneumoniae* infection and the impact of antimicrobial and adjunctive therapies. Infection control and hospital epidemiology: the official journal of the Society of Hospital Epidemiologists of America. 2008; 29(12):1099-106. doi: 10.1086/592412. PubMed PMID: 18973455.

4. Yigit H, Queenan A M, Anderson G J, Domenech-Sanchez A, Biddle J W, Steward C D, et al. Novel carbapenem-hydrolyzing beta-lactamase, KPC-1, from a carbapenem-resistant strain of *Klebsiella pneumoniae*. Antimicrob Agents Chemother. 2001; 45(4):1151-61. Epub 2001/03/21. doi: 10.1128/AAC.45.4.1151-1161.2001. PubMed PMID: 11257029; PubMed Central PMCID: PMC90438.

5. Brink A J, Coetzee J, Clay C G, Sithole S, Richards G A, Poirel L, et al. Emergence of New Delhi metallo-beta-lactamase (NDM-1) and *Klebsiella pneumoniae* carbapenemase (KPC-2) in South Africa. J Clin Microbiol. 2012; 50(2):525-7. doi: 10.1128/JCM.05956-11. PubMed PMID: 22116157; PubMed Central PMCID: PMC3264190.

6. Munoz-Price L S, Poirel L, Bonomo R A, Schwaber M J, Daikos G L, Cormican M, et al. Clinical epidemiology of the global expansion of *Klebsiella pneumoniae* carbapenemases. The Lancet infectious diseases. 2013; 13(9):785-96. doi: 10.1016/S1473-3099(13)70190-7. PubMed PMID: 23969216.

7. Chen L F, Anderson D J, Paterson D L. Overview of the epidemiology and the threat of *Klebsiella pneumoniae* carbapenemases (KPC) resistance. Infection and drug resistance. 2012; 5:133-41. doi: 10.2147/IDR.S26613. PubMed PMID: 23055754; PubMed Central PMCID: PMC3460674.

8. Bialek-Davenet S, Criscuolo A, Ailloud F, Passet V, Jones L, Delannoy-Vieillard A S, et al. Genomic definition of hypervirulent and multidrug-resistant *Klebsiella pneumoniae* clonal groups. Emerg Infect Dis. 2014; 20(11):1812-20. doi: 10.3201/eid2011.140206. PubMed PMID: 25341126; PubMed Central PMCID: PMC4214299.

9. Voulgari E, Gartzonika C, Vrioni G, Politi L, Priavali E, Levidiotou-Stefanou S, et al. The Balkan region: NDM-1-producing *Klebsiella pneumoniae* ST11 clonal strain causing outbreaks in Greece. J Antimicrob Chemother. 2014. doi: 10.1093/jac/dku105. PubMed PMID: 24739146.

10. Pena I, Picazo J J, Rodriguez-Avial C, Rodriguez-Avial I. Carbapenemase-producing Enterobacteriaceae in a tertiary hospital in Madrid, Spain: high percentage of colistin resistance among VIM-1-producing *Klebsiella pneumoniae* ST11 isolates. Int J Antimicrob Agents. 2014. doi: 10.1016/j.ijantimicag.2014.01.021. PubMed PMID: 24657043.

11. Lascols C, Peirano G, Hackel M, Laupland K B, Pitout J D. Surveillance and molecular epidemiology of *Klebsiella pneumoniae* isolates that produce carbapenemases: first report of OXA-48-like enzymes in North America. Antimicrob Agents Chemother. 2013; 57(1):130-6. doi: 10.1128/AAC.01686-12. PubMed PMID: 23070171; PubMed Central PMCID: PMC3535978.

12. Woodford N, Turton J F, Livermore D M. Multiresistant Gram-negative bacteria: the role of high-risk clones in the dissemination of antibiotic resistance. FEMS microbiology reviews. 2011; 35(5):736-55. doi: 10.1111/j.1574-6976.2011.00268.x. PubMed PMID: 21303394.

13. Grundmann H, Livermore D M, Giske C G, Canton R, Rossolini G M, Campos J, et al. Carbapenem-non-susceptible Enterobacteriaceae in Europe: conclusions from a meeting of national experts. Euro surveillance: bulletin Europeen sur les maladies transmissibles=European communicable disease bulletin. 2010; 15(46). PubMed PMID: 21144429.

14. Chmelnitsky I, Shklyar M, Hermesh O, Navon-Venezia S, Edgar R, Carmeli Y. Unique genes identified in the epidemic extremely drug-resistant KPC-producing *Klebsiella pneumoniae* sequence type 258. J Antimicrob Chemother. 2013; 68(1):74-83. Epub 2012/10/09. doi: 10.1093/jac/dks370. PubMed PMID: 23042812.

15. Deleo F R, Chen L, Porcella S F, Martens C A, Kobayashi S D, Porter A R, et al. Molecular dissection of the evolution of carbapenem-resistant multilocus sequence type 258 *Klebsiella pneumoniae*. Proc Natl Acad Sci USA. 2014. Epub 2014/03/19. doi: 10.1073/pnas.1321364111. PubMed PMID: 24639510.

16. Adler A, Khabra E, Chmelnitsky I, Giakkoupi P, Vatopoulos A, Mathers A J, et al. Development and validation of a multiplex PCR assay for identification of the epidemic ST-258/512 KPC-producing *Klebsiella pneumoniae* clone. Diagn Microbiol Infect Dis. 2014; 78(1):12-5. doi: 10.1016/j.diagmicrobio.2013.10.003. PubMed PMID: 24231383.

17. Gaiarsa S, Comandatore F, Gaibani P, Corbella M, Dalla Valle C, Epis S, et al. Genomic epidemiology of *Klebsiella pneumoniae*: the Italian scenario, and novel insights into the origin and global evolution of resistance to carbapenem antibiotics. Antimicrob Agents Chemother. 2014. doi: 10.1128/AAC.04224-14. PubMed PMID: 25367909.

18. Wyres K L, Gorrie C, Edwards D J, Wertheim H F, Hsu L Y, Van Kinh N, et al. Extensive capsule locus variation and large-scale genomic recombination within the *Klebsiella pneumoniae* clonal group 258. Genome Biol Evol. 2015. doi: 10.1093/gbe/evv062. PubMed PMID: 25861820.

19. Croucher N J, Harris S R, Grad Y H, Hanage W P. Bacterial genomes in epidemiology—present and future. Philosophical transactions of the Royal Society of London Series B, Biological sciences. 2013; 368(1614): 20120202. doi: 10.1098/rstb.2012.0202. PubMed PMID: 23382424; PubMed Central PMCID: PMC3678326.

20. Chen L, Mathema B, Pitout J D, DeLeo F R, Kreiswirth B N. Epidemic *Klebsiella pneumoniae* ST258 Is a Hybrid Strain. MBio. 2014; 5(3). doi: 10.1128/mBio.01355-14. PubMed PMID: 24961694; PubMed Central PMCID: PMC4073492.

21. Navon-Venezia S, Leavitt A, Schwaber M J, Rasheed J K, Srinivasan A, Patel J B, et al. First report on a hyperepidemic clone of KPC-3-producing *Klebsiella pneumoniae* in Israel genetically related to a strain causing outbreaks in the United States. Antimicrob Agents Chemother. 2009; 53(2):818-20. Epub 2008/11/26. doi: 10.1128/AAC.00987-08. PubMed PMID: 19029323; PubMed Central PMCID: PMC2630632.

22. Woodford N, Tierno P M, Jr., Young K, Tysall L, Palepou M F, Ward E, et al. Outbreak of *Klebsiella pneumoniae* producing a new carbapenem-hydrolyzing class A beta-lactamase, KPC-3, in a New York Medical Center. Antimicrob Agents Chemother. 2004; 48(12):4793-9. Epub 2004/11/25. doi: 48/12/4793 [pii]10.1128/AAC.48.12.4793-4799.2004. PubMed PMID: 15561858; PubMed Central PMCID: PMC529220.

23. Snitkin E S, Zelazny A M, Thomas P J, Stock F, Group NCSP, Henderson D K, et al. Tracking a hospital outbreak of carbapenem-resistant *Klebsiella pneumoniae* with whole-genome sequencing. Science translational medicine.

2012; 4(148):148ra16. doi: 10.1126/scitranslmed.3004129. PubMed PMID: 22914622; PubMed Central PMCID: PMC3521604.

24. Huntington P, Coatsworth N, Hardiman R, Hudson B, Kotsiou G, Fernandes C, editors. *Klebsiella pneumoniae* carbapenemase in Australia: detection of a KPC-producing clinical isolate at a Sydney hospital. The Australian Society for Microbiology 2011 Annual Conference; 2011; Hobart, Tasmania, Australia: The Australian Society for Microbiology 2011 Annual Conference.
25. Osterblad M, Kirveskari J, Koskela S, Tissari P, Vuorenoja K, Hakanen A J, et al. First isolations of KPC-2-carrying ST258 *Klebsiella pneumoniae* strains in Finland, June and August 2009. Euro surveillance: bulletin Europeen sur les maladies transmissibles=European communicable disease bulletin. 2009; 14(40). PubMed PMID: 19822122.
26. Hammerum A M, Hansen F, Lester C H, Jensen K T, Hansen D S, Dessau R B. Detection of the first two *Klebsiella pneumoniae* isolates with sequence type 258 producing KPC-2 carbapenemase in Denmark. Int J Antimicrob Agents. 2010; 35(6):610-2. doi: 10.1016/j.ijantimicag.2010.01.024. PubMed PMID: 20206479.
27. Giani T, D'Andrea M M, Pecile P, Borgianni L, Nicoletti P, Tonelli F, et al. Emergence in Italy of *Klebsiella pneumoniae* sequence type 258 producing KPC-3 Carbapenemase. J Clin Microbiol. 2009; 47(11):3793-4. doi: 10.1128/JCM.01773-09. PubMed PMID: 19759220; PubMed Central PMCID: PMC2772625.
28. Cuzon G, Naas T, Nordmann P. Functional characterization of Tn4401, a Tn3-based transposon involved in blaKPC gene mobilization. Antimicrob Agents Chemother. 2011; 55(11):5370-3. Epub 2011/08/17. doi: AAC.05202-11 [pii]10.1128/AAC.05202-11. PubMed PMID: 21844325; PubMed Central PMCID: PMC3195030.
29. Naas T, Cuzon G, Truong H V, Nordmann P. Role of ISKpn7 and deletions in blaKPC gene expression. Antimicrob Agents Chemother. 2012. Epub 2012/06/27. doi: AAC.00334-12 [pii] 10.1128/AAC.00334-12. PubMed PMID: 22733068.
30. Endimiani A, Hujer A M, Perez F, Bethel C R, Hujer K M, Kroeger J, et al. Characterization of blaKPC-containing *Klebsiella pneumoniae* isolates detected in different institutions in the Eastern USA. J Antimicrob Chemother. 2009; 63(3):427-37. Epub 2009/01/22. doi: 10.1093/jac/dkn547. PubMed PMID: 19155227; PubMed Central PMCID: PMC2640158.
31. Gomez S A, Pasteran F G, Faccone D, Tijet N, Rapoport M, Lucero C, et al. Clonal dissemination of *Klebsiella pneumoniae* ST258 harbouring KPC-2 in Argentina. Clin Microbiol Infect. 2011; 17(10):1520-4. doi: 10.11111.1469-0691.2011.03600.x. PubMed PMID: 21851480.
32. Garcia-Femandez A, Villa L, Carta C, Venditti C, Giordano A, Venditti M, et al. *Klebsiella pneumoniae* ST258 producing KPC-3 identified in Italy carries novel plasmids and OmpK36/OmpK35 porin variants. Antimicrob Agents Chemother. 2012. Epub 2012/01/19. doi: AAC.05308-11 [pii] 10.1128/AAC.05308-11. PubMed PMID: 22252815.
33. Leavitt A, Chmelnitsky I, Carmeli Y, Navon-Venezia S. Complete nucleotide sequence of KPC-3-encoding plasmid pKpQIL in the epidemic *Klebsiella pneumoniae* sequence type 258. Antimicrob Agents Chemother. 2010; 54(10):4493-6. Epub 2010/08/11. doi: AAC.00175-10 [pii] 10.1128/AAC.00175-10. PubMed PMID: 20696875; PubMed Central PMCID: PMC2944570.
34. Chen L, Chavda K D, Melano R G, Jacobs M R, Koll B, Hong T, et al. Comparative Genomic Analysis of KPC-Encoding pKpQIL-Like Plasmids and Their Distribution in New Jersey and New York Hospitals. Antimicrob Agents Chemother. 2014; 58(5):2871-7. doi: 10.1128/AAC.00120-14. PubMed PMID: 24614371.
35. Adler A, Paikin S, Sterlin Y, Glick J, Edgar R, Aronov R, et al. A Swordless Knight: the epidemiology and molecular characteristics of the blaKPC-negative sequence-type 258 *Klebsiella pneumoniae* clone. J Clin Microbiol. 2012. Epub 2012/07/21. doi: JCM.00987-12 [pii] 10.1128/JCM.00987-12. PubMed PMID: 22814467.
36. Frasson I, Lavezzo E, Franchin E, Toppo S, Barzon L, Cavallaro A, et al. Antimicrobial treatment and containment measures for an extremely drug-resistant *Klebsiella pneumoniae* ST101 isolate carrying pKPN101-IT, a novel fully sequenced bla(KPC-2) plasmid. J Clin Microbiol. 2012; 50(11):3768-72. Epub 2012/09/14. doi: 10.1128/JCM.01892-12 JCM.01892-12 [pii]. PubMed PMID: 22972824; PubMed Central PMCID: PMC3486238.
37. Mataseje L F, Boyd D A, Willey B M, Prayitno N, Kreiswirth N, Gelosia A, et al. Plasmid comparison and molecular analysis of *Klebsiella pneumoniae* harbouring bla(KPC) from New York City and Toronto. J Antimicrob Chemother. 2011; 66(6):1273-7. Epub 2011/03/17. doi: dkr092 [pii] 10.1093/jac/dkr092. PubMed PMID: 21406433.
38. Jiang Y, Yu D, Wei Z, Shen P, Zhou Z, Yu Y. Complete nucleotide sequence of *Klebsiella pneumoniae* multidrug resistance plasmid pKPO48, carrying blaKPC-2, blaDHA-1, qnrB4, and armA. Antimicrob Agents Chemother. 2010; 54(9):3967-9. Epub 2010/06/16. doi: AAC.00137-10 [pii] 10.1128/AAC.00137-10. PubMed PMID: 20547789; PubMed Central PMCID: PMC2934982.
39. Almeida A C, de Sa Cavalcanti F L, Vilela M A, Gales A C, de Morais M A, Jr., Camargo de Morals M M. *Escherichia coli* ST502 and *Klebsiella pneumoniae* ST11 sharing an IncW plasmid harbouring the bla(KPC-2) gene in an Intensive Care Unit patient. Int J Antimicrob Agents. 2012; 40(4):374-6. Epub 2012/07/24. doi: 10.1016/j.ijantimicag.2012.05.022. PubMed PMID: 22817916.
40. Lery L M, Frangeul L, Tomas A, Passet V, Almeida A S, Bialek-Davenet S, et al. Comparative analysis of *Klebsiella pneumoniae* genomes identifies a phospholipase D family protein as a novel virulence factor. BMC Biol. 2014; 12:41. doi: 10.1186/1741-7007-12-41. PubMed PMID: 24885329; PubMed Central PMCID: PMC4068068.
41. Perera I C, Grove A. Molecular mechanisms of ligand-mediated attenuation of DNA binding by MarR family transcriptional regulators. Journal of molecular cell biology. 2010; 2(5):243-54. doi: 10.1093/jmcb/mjq021. PubMed PMID: 20716550.
42. Grkovic S, Brown M H, Skurray R A. Regulation of bacterial drug export systems. Microbiology and molecular biology reviews: MMBR. 2002; 66(4):671-701, table of contents. PubMed PMID: 12456787; PubMed Central PMCID: PMC134658.
43. Li X Z, Plesiat P, Nikaido H. The challenge of efflux-mediated antibiotic resistance in Gram-negative bacteria. Clin Microbiol Rev. 2015; 28(2):337-418. doi: 10.1128/CMR.00117-14. PubMed PMID: 25788514.
44. Hao Z, Lou H, Zhu R, Zhu J, Zhang D, Zhao B S, et al. The multiple antibiotic resistance regulator MarR is a copper sensor in *Escherichia coli*. Nature chemical biology. 2014; 10(1):21-8. doi: 10.1038/nchembio.1380. PubMed PMID: 24185215.

45. Wang X, Chen H, Zhang Y, Wang Q, Zhao C, Li H, et al. Genetic characterisation of clinical *Klebsiella pneumoniae* isolates with reduced susceptibility to tigecycline: Role of the global regulator RamA and its local repressor RamR. Int J Antimicrob Agents. 2015. doi: 10.1016/j.ijantimicag.2014.12.022. PubMed PMID: 25681067.

46. De Majumdar S, Yu J, Fookes M, McAteer S P, Uobet E, Finn S, et al. Elucidation of the RamA Regulon in *Klebsiella pneumoniae* Reveals a Role in LPS Regulation. PLoS pathogens. 2015; 11(1):e1004627. doi: 10.1371/joumal.ppat.1004627. PubMed PMID: 25633080; PubMed Central PMCID: PMC4310594.

47. Zhong X, Xu H, Chen D, Zhou H, Hu X, Cheng G. First emergence of acrAB and oqxAB mediated tigecycline resistance in clinical isolates of *Klebsiella pneumoniae* pre-dating the use of tigecycline in a Chinese hospital. PLoS One. 2014; 9(12):e115185. doi: 10.1371/journal-.pone.0115185. PubMed PMID: 25503276; PubMed Central PMCID: PMC4264890.

48. Hansen L H, Johannesen E, Burmolle M, Sorensen A H, Sorensen S J. Plasmid-encoded multidrug efflux pump conferring resistance to olaquindox in *Escherichia coli*. Antimicrob Agents Chemother. 2004; 48(9):3332-7. doi: 10.1128/AAC.48.9.3332-3337.2004. PubMed PMID: 15328093; PubMed Central PMCID: PMC514751.

49. Perez F, Rudin S D, Marshall S H, Coakley P, Chen L, Kreiswirth B N, et al. OqxAB, a quinolone and olaquindox efflux pump, is widely distributed among multidrug-resistant *Klebsiella pneumoniae* isolates of human origin. Antimicrob Agents Chemother. 2013; 57(9):4602-3. doi: 10.1128/AAC.00725-13. PubMed PMID: 23817374; PubMed Central PMCID: PMC3754307.

50. Bialek-Davenet S, Lavigne J P, Guyot K, Mayer N, Tournebize R, Brisse S, et al. Differential contribution of AcrAB and OqxAB efflux pumps to multidrug resistance and virulence in *Klebsiella pneumoniae*. J Antimicrob Chemother. 2015; 70(1):81-8. doi: 10.1093/jac/dku340. PubMed PMID: 25193085.

51. Veleba M, Higgins P G, Gonzalez G, Seifert H, Schneiders T. Characterization of RarA, a novel AraC family multidrug resistance regulator in *Klebsiella pneumoniae*. Antimicrob Agents Chemother. 2012; 56(8):4450-8. doi: 10.1128/AAC.00456-12. PubMed PMID: 22644028; PubMed Central PMCID: PMC3421627.

52. Frank C G, Reguerio V, Rother M, Moranta D, Maeurer A P, Garmendia J, et al. *Klebsiella pneumoniae* targets an EGF receptor-dependent pathway to subvert inflammation. Cellular microbiology. 2013; 15(7):1212-33. doi: 10.1111/cmi.12110. PubMed PMID: 23347154.

53. Segura M. Fisher scientific award lecture—the capsular polysaccharides of Group B *Streptococcus* and *Streptococcus suis* differently modulate bacterial interactions with dendritic cells. Canadian journal of microbiology. 2012; 58(3):249-60. doi: 10.1139/w2012-003. PubMed PMID: 22356626.

54. Lin J, Huang S, Zhang Q. Outer membrane proteins: key players for bacterial adaptation in host niches. Microbes and infection/Institut Pasteur. 2002; 4(3):325-31. PubMed PMID: 11909743.

55. March C, Cano V, Moranta D, Llobet E, Perez-Gutierrez C, Tomas J M, et al. Role of bacterial surface structures on the interaction of *Klebsiella pneumoniae* with phagocytes. PLoS One. 2013; 8(2):e56847. doi: 10.1371/journal.pone.0056847. PubMed PMID: 23457627; PubMed Central PMCID: PMC3574025.

56. Smith S G, Mahon V, Lambert M A, Fagan R P. A molecular Swiss army knife: OmpA structure, function and expression. FEMS microbiology letters. 2007; 273 (1):1-11. doi: 10.1111/j.1574-6968.2007.00778.x. PubMed PMID: 17559395.

57. Garcia-Sureda L, Domenech-Sanchez A, Barbier M, Juan C, Gasco J, Alberti S. OmpK26, a novel porin associated with carbapenem resistance in *Klebsiella pneumoniae*. Antimicrob Agents Chemother. 2011; 55(10): 4742-7. doi: 10.1128/AAC.00309-11. PubMed PMID: 21807980; PubMed Central PMCID: PMC3186958.

58. Kitchel B, Rasheed J K, Endimiani A, Hujer A M, Anderson K F, Bonomo R A, et al. Genetic factors associated with elevated carbapenem resistance in KPC-producing *Klebsiella pneumoniae*. Antimicrob Agents Chemother. 2010; 54(10):4201-7. Epub 2010/07/28. doi: AAC.00008-10 [pii] 10.1128/AAC.00008-10. PubMed PMID: 20660684; PubMed Central PMCID: PMC2944623.

59. Domenech-Sanchez A, Martinez-Martinez L, Hernandez-Alles S, del Carmen Conejo M, Pascual A, Tomas J M, et al. Role of *Klebsiella pneumoniae* OmpK35 porin in antimicrobial resistance. Antimicrob Agents Chemother. 2003; 47(10):3332-5. PubMed PMID: 14506051; PubMed Central PMCID: PMC201126.

60. Kaczmarek F M, Dib-Hajj F, Shang W, Gootz T D. High-level carbapenem resistance in a *Klebsiella pneumoniae* clinical isolate is due to the combination of bla(ACT-1) beta-lactamase production, porin OmpK35/36 insertional inactivation, and down-regulation of the phosphate transport porin phoe. Antimicrob Agents Chemother. 2006; 50(10):3396-406. doi: 10.1128/AAC.00285-06. PubMed PMID: 17005822; PubMed Central PMCID: PMC1610099.

61. Croucher N J, Klugman K P. The emergence of bacterial "hopeful monsters". MBio. 2014; 5(4):e01550-14. doi: 10.1128/mBio.01550-14. PubMed PMID: 25073645; PubMed Central PMCID: PMC4128365.

62. Souli M, Galani I, Antoniadou A, Papadomichelakis E, Poulakou G, Panagea T, et al. An outbreak of infection due to beta-Lactamase *Klebsiella pneumoniae* Carbapenemase 2-producing *K. pneumoniae* in a Greek University Hospital: molecular characterization, epidemiology, and outcomes. Clin Infect Dis. 2010; 50(3):364-73. doi: 10.1086/649865. PubMed PMID: 20041768.

63. America TSfHEo. Large Veteran Health Administration Study Shows 'Last Resort' Antibiotics Use on the Rise Dallas, Tex.2011 [cited 2014 Aug. 12].

64. Tsai Y K, Fung C P, Lin J C, Chen J H, Chang F Y, Chen T L, et al. *Klebsiella pneumoniae* outer membrane porins OmpK35 and OmpK36 play roles in both antimicrobial resistance and virulence. Antimicrob Agents Chemother. 2011; 55(4):1485-93. doi: 10.1128/AAC.01275-10. PubMed PMID: 21282452; PubMed Central PMCID: PMC3067157.

65. Holt K. SRST2 Short Read Sequence Typing for Bacterial Pathogens: GitHub; 2013 [updated Feb. 6, 2014; cited 2014 Mar. 1].

66. McKenna A, Hanna M, Banks E, Sivachenko A, Cibulskis K, Kernytsky A, et al. The Genome Analysis Toolkit: a MapReduce framework for analyzing next-generation DNA sequencing data. Genome Res. 2010; 20(9):1297-303. doi: 10.1101/gr.107524.110. PubMed PMID: 20644199; PubMed Central PMCID: PMC2928508.

67. Tamura K, Peterson D, Peterson N, Stecher G, Nei M, Kumar S. MEGA5: molecular evolutionary genetics analysis using maximum likelihood, evolutionary distance, and maximum parsimony methods. Mol Biol Evol. 2011; 28(10):2731-9. Epub 2011/05/07. doi: msr121 [pi] 10.1093/molbev/msr121. PubMed PMID: 21546353; PubMed Central PMCID: PMC3203626.

68. Paradis E, Claude J, Strimmer K. APE: Analyses of Phylogenetics and Evolution in R language. Bioinformatics. 2004; 20(2):289-90. PubMed PMID: 14734327.

69. Letunic I, Bork P. Interactive Tree Of Life v2: online annotation and display of phylogenetic trees made easy. Nucleic acids research. 2011; 39 (Web Server issue): W475-8. doi: 10.1093/nar/gkr201. PubMed PMID: 21470960; PubMed Central PMCID: PMC3125724.

70. Drummond A J, Suchard M A, Xie D, Rambaut A. Bayesian phylogenetics with BEAUti and the BEAST 1.7. Mol Biol Evol. 2012; 29(8):1969-73. Epub 2012/03/01. doi: 10.1093/molbev/mss075. PubMed PMID: 22367748; PubMed Central PMCID: PMC3408070.

71. Carattoli A, Zankari E, Garcia-Femandez A, Volby Larsen M, Lund O, Villa L, et al. PlasmidFinder and pMLST: in silico detection and typing of plasmids. Antimicrob Agents Chemother. 2014. doi: 10.1128/AAC.02412-14. PubMed PMID: 24777092.

72. Zankari E, Hasman H, Cosentino S, Vestergaard M, Rasmussen S, Lund O, et al. Identification of acquired antimicrobial resistance genes. J Antimicrob Chemother. 2012; 67(11):2640-4. doi: 10.1093/jac/dks261. PubMed PMID: 22782487; PubMed Central PMCID: PMC3468078.

73. Bankevich A, Nurk S, Antipov D, Gurevich A A, Dvorkin M, Kulikov A S, et al. SPAdes: a new genome assembly algorithm and its applications to single-cell sequencing. Journal of computational biology: a journal of computational molecular cell biology. 2012; 19(5):455-77. doi: 10.1089/cmb.2012.0021. PubMed PMID: 22506599; PubMed Central PMCID: PMC3342519.

74. Bolger A M, Lohse M, Usadel B. Trimmomatic: A flexible trimmer for Illumina Sequence Data. Bioinformatics. 2014. doi: 10.1093/bioinformatics/btul70. PubMed PMID: 24695404.

75. Geneious. Available from Biomatters Ltd. 2013.

76. Pan Y J, Lin T L, Lin Y T, Su P A, Chen C T, Hsieh P F, et al. Identification of Capsular Types in Carbapenem-Resistant *Klebsiella pneumoniae* Strains by wzc Sequencing and Implications for Capsule Depolymerase Treatment. Antimicrob Agents Chemother. 2015; 59(2):1038-47. doi: 10.1128/AAC.03560-14. PubMed PMID: 25451047.

77. Brisse S, Passet V, Haugaard A B, Babosan A, Kassis-Chikhani N, Struve C, et al. wzi Gene sequencing, a rapid method for determination of capsular type for *Klebsiella* strains. J Clin Microbiol. 2013; 51(12):4073-8. doi: 10.1128/JCM.01924-13. PubMed PMID: 24088853; PubMed Central PMCID: PMC3838100.

78. Wilkinson S P, Grove A. Ligand-responsive transcriptional regulation by members of the MarR family of winged helix proteins. Current issues in molecular biology. 2006; 8(1):51-62. PubMed PMID: 16450885.

What is claimed is:

1. A method of detecting carbapenem-resistant Enterobacteriaceae in a sample, the method comprising the steps of:

adding to a mixture comprising the sample a first oligonucleotide consisting of SEQ ID NO: 1, a second oligonucleotide consisting of SEQ ID NO: 2, and a third oligonucleotide consisting of SEQ ID NO: 3;

subjecting the mixture to conditions that allow nucleic acid amplification; and detecting the carbapenem-resistant Enterobacteriaceae in the sample by detecting nucleic acid amplification in the mixture.

2. The method of claim 1, wherein the nucleic acid amplification comprises calculating a Ct value.

3. The method of claim 1, wherein the sample comprises an environmental sample.

4. The method of claim 1, wherein the sample is derived from a subject, wherein the subject is human, an animal, an insect, a plant, or a bacteria.

5. The method of claim 4, wherein the sample comprises sputum.

6. The method of claim 1, wherein the carbapenem-resistant Enterobacteriaceae is *Klebsiella pneumoniae.*

7. A method of detecting a *Klebsiella pneumoniae* carbapenemase (KPC)-producing isolate in a sample, the method comprising the steps of:

adding to a first mixture comprising the sample a first oligonucleotide consisting of SEQ ID NO: 1, a second oligonucleotide consisting of SEQ ID NO: 2, and a third oligonucleotide consisting of SEQ ID NO: 3;

adding to a second mixture comprising the sample a fourth oligonucleotide consisting of SEQ ID NO: 1, a fifth oligonucleotide consisting of SEQ ID NO: 2, and a sixth oligonucleotide consisting of SEQ ID NO: 4;

subjecting the first mixture and second mixture to conditions that allow nucleic acid amplification; and detecting the KPC-producing isolate in the sample by detecting the nucleic acid amplification in the first mixture and second mixture, wherein nucleic acid amplification in the first mixture indicates presence of the KPC-producing isolate.

8. The method of claim 7, wherein nucleic acid amplification in the second mixture indicates absence of the KPC-producing isolate.

9. The method of claim 7, wherein the KPC-producing isolate is ST258.

10. The method of claim 7, wherein detecting the nucleic acid amplification comprises calculating a Ct value.

11. The method of claim 10, wherein if the ST258 strain of the KPC-producing isolate is present in the sample, the Ct value in the first mixture will be lower than the Ct value in the second mixture.

12. The method of claim 7, wherein the sample comprises an environmental sample.

13. The method of claim 7, wherein the sample is derived from a subject, wherein the subject is a human, an animal, an insect, a plant, or a bacteria.

14. The method of claim 13, wherein the sample comprises sputum.

15. A method of detecting a *Klebsiella pneumoniae* ST258 strain in a sample, the method comprising the steps of:

adding to a mixture comprising the sample a first oligonucleotide consisting of SEQ ID NO: 1, a second oligonucleotide consisting of SEQ ID NO: 2, a third oligonucleotide consisting of SEQ ID NO: 3, and a fourth oligonucleotide consisting of SEQ ID NO: 4;

subjecting the mixture to conditions that allow nucleic acid amplification; and detecting the *Klebsiella pneumoniae* ST258 strain in the sample by detecting nucleic acid amplification of SEQ ID NO: 3 in the mixture.

16. The method of claim 15, wherein the sample comprises an environmental sample.

17. The method of claim 15, wherein the sample is from a subject, wherein the subject is human, an animal, an insect, a plant, or a bacteria.

18. The method of claim 17, wherein if the *Klebsiella pneumoniae* ST258 strain is detected in the subject the method further comprises of the step of administering to the subject a therapeutically effective amount of an antibiotic to which the *Klebsiella pneumoniae* ST258 strain is sensitive.

* * * * *